US009474747B2

(12) United States Patent
Albrecht et al.

(10) Patent No.: US 9,474,747 B2
(45) Date of Patent: Oct. 25, 2016

(54) MUSCARINIC ANTAGONISTS AND COMBINATIONS THEREOF FOR THE TREATMENT OF AIRWAY DISEASE IN HORSES

(71) Applicant: Boehringer Ingelheim Vetmedica GmbH, Ingelheim am Rhein (DE)

(72) Inventors: Balazs Albrecht, Sprendlingen (DE); Michael Aven, Mainz (DE); Janine Lamar, Ingelheim am Rhein (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/740,582

(22) Filed: Jun. 16, 2015

(65) Prior Publication Data

US 2015/0366855 A1 Dec. 24, 2015

(30) Foreign Application Priority Data

Jun. 18, 2014 (EP) .................................... 14172925

(51) Int. Cl.
| | | |
|---|---|---|
| A61K 31/46 | (2006.01) | |
| A61K 35/06 | (2006.01) | |
| A61M 15/00 | (2006.01) | |
| A61K 31/58 | (2006.01) | |

(52) U.S. Cl.
CPC .............. *A61K 31/46* (2013.01); *A61K 31/58* (2013.01); *A61K 35/06* (2013.01); *A61M 15/009* (2013.01); *A61M 2250/00* (2013.01)

(58) Field of Classification Search
None
See application file for complete search history.

(56) References Cited

U.S. PATENT DOCUMENTS

| | | | |
|---|---|---|---|
| 5,954,049 A | 9/1999 | Foley et al. | |
| 6,264,923 B1 | 7/2001 | Oliver et al. | |
| 6,706,726 B2 | 3/2004 | Meissner et al. | |
| 7,244,742 B2 | 7/2007 | Pieper et al. | |
| 2004/0266869 A1 | 12/2004 | Montague et al. | |
| 2006/0069073 A1 | 3/2006 | Pieper et al. | |
| 2006/0110329 A1 | 5/2006 | Pieper | |
| 2006/0293293 A1 | 12/2006 | Muller et al. | |
| 2007/0117783 A1 | 5/2007 | Brueck-Scheffler | |
| 2008/0041369 A1 | 2/2008 | Radau et al. | |
| 2008/0041370 A1 | 2/2008 | Radau et al. | |
| 2012/0058980 A1 | 3/2012 | Radau et al. | |
| 2014/0179651 A1 | 6/2014 | Albrecht et al. | |
| 2015/0313918 A1 | 11/2015 | Albrecht et al. | |

FOREIGN PATENT DOCUMENTS

| | | |
|---|---|---|
| WO | 9712687 A1 | 4/1997 |
| WO | 0232899 A1 | 4/2002 |
| WO | 2004022058 A1 | 3/2004 |
| WO | 2004023984 A2 | 3/2004 |
| WO | 2005009426 A1 | 2/2005 |
| WO | 2006056527 A1 | 6/2006 |
| WO | 2010149280 A1 | 12/2010 |
| WO | 2014096115 A1 | 6/2014 |
| WO | 2015193213 A1 | 12/2015 |

OTHER PUBLICATIONS

Belvisi et al., "Preclinical Profile of Ciclesonide, a Novel Corticosteroid for the Treatment of Asthma". The Journal of Pharmacology and Experimental Therapeutics, vol. 314, No. 2, 2005, pp. 568-574.
Couetil et al., "Inflammatory Airway Disease of Horses"., Journal of Veterinary Internal Medicine, vol. 21, 2007, pp. 356-361.
Dauvillier et al., "Effect of Long-Term Fluticasone Treatment on Immune Function in Horses with Heaves". Journal of Veterinary Internal Medicine, vol. 25, No. 3, pp. 549-557, 2011.
Dietzel et al., "Ciclesonide: An On-Site-Activated Steroid". New Drugs for Asthma, Allergy and COPD. Progress in Respiratory Research, Basel, Karger, vol. 31, 2001, pp. 91-93.
Grahnén et al., "A dose-response study comparing supression of plasma cortisol influenced by fluticasone propionate from Diskhaler and budesonide from Turbuhaler"., European Journal of Clinical Pharmacology, vol. 52, 1997, pp. 261-267.
International Search Report and Written Opinion for PCT/EP2015/063265 mailed Jul. 28, 2015.
Kutasi et al., "Diagnostic Approaches for the Assessment of Equine Chronic Pulmonary Disorders". Journal of Equine Veterinary Science, vol. 31, 2011, pp. 400-410.
Matera et al., "Innervation of Equine Airways". Pulmonary Pharmacology & Therapeutics, vol. 15, 2002, pp. 503-511.
Robinson et al., "Fluticasone Propionate Aerosol is More Effective for Prevention than Treatment of Recurrent Airway Obstruction". Journal of Veterinary Internal Medicine, vol. 23, 2009, pp. 1247-1253.
Robinson et al., "The airway response of horses with recurrent airway obstruction (heaves) to aerosol administration of ipratropium bromide". Equine Veterinary Journal, vol. 25, No. 4, 1993, pp. 299-303.
Holmes et al., "Horse carboxylesterases: Evidence for six CES1 and four families of CES genes on chromosome 3". Comparative Biochemistry and Physiology, Part D, vol. 4, 2009, pp. 54-65.
Mutch et al., "The role of esterases in the metabolish of ciclesonide to desisobutyryl-ciclesonide in human tissue". Biochemical Pharmacology, vol. 73, 2007, pp. 1657-1664.
Robinson, N.E. "International Workshop on Equine Chronic Airway Disease. Michigan State University, Jun. 16-18, 2000". Equine Veterinary Journal vol. 33, No. 1, 2001, pp. 5-19.
Leclere et al., "Invited Review Series: Cutting Edge Technologies". Official Journal of the Asian Pacific Society of Respirology, Respirology, vol. 16, 2011, pp. 1027-1046.

*Primary Examiner* — Kristin Vajda
(74) *Attorney, Agent, or Firm* — Michael P. Morris; Joyce L. Morrison

(57) ABSTRACT

The invention relates to the field of medicine, in particular to the field of veterinary medicine. The invention specifically relates to muscarinic antagonists (including long acting muscarinic antagonists (LAMAs)) for the treatment of airway disease, such as pulmonary disease, preferably recurrent airway obstruction (RAO), summer pasture associated obstructive pulmonary disease (SPAOPD), and inflammatory airway disease (IAD) in animals, preferably equines such as horses.

31 Claims, 11 Drawing Sheets

MUSCARINIC ANTAGONISTS AND COMBINATIONS THEREOF FOR THE TREATMENT OF AIRWAY DISEASE IN HORSES

FIELD OF THE INVENTION

The invention relates to the field of medicine, in particular to the field of veterinary medicine. The invention specifically relates to muscarinic antagonists (including long acting muscarinic antagonists (LAMAs)) for the treatment of airway disease, such as pulmonary disease, preferably recurrent airway obstruction (RAO), summer pasture associated obstructive pulmonary disease (SPAOPD), and inflammatory airway disease (IAD) in animals, preferably equines such as horses.

BACKGROUND INFORMATION

Equine airway disease is a prominent disease in many horses. It can be divided into the diseases of the upper and lower airways. There are a number of equine lower airway diseases with noninfectious origin such as RAO (or heaves or equine chronic obstructive pulmonary disease), IAD, SPAOPD and exercise induced pulmonary hemorrhage (EIPH). The latter is typically diagnosed in racehorses. RAO, IAD and SPAOPD are diseases with an allergic background. Rarely diagnosed additional lower airway disorders are granulomatous, neoplastic and interstitial pneumonias. The infectious diseases of the lower airway include bronchitis, pneumonia, pleuritis or a combination of these caused by viral, bacterial, fungal and parasitic agents (Kutasi et al., 2011).

Common phenotypic manifestations of airway disease in horses include coughing, nasal discharge, increased respiratory effort and poor performance or exercise intolerance. Additionally, fever, depression, decreased appetite and weight loss can be observed in infectious airway diseases (Couetil et al., 2007 and Kutasi et al., 2011).

Equine airway diseases with an allergic background cannot be cured but only kept asymptomatic. The known therapies for these horses include changes in the environment and the administration of different drugs. The aim of the change in the stable environment is to improve airway quality and to reduce the allergen exposure of the horses, which might trigger the exacerbations of RAO, SPAOPD and IAD. The following drugs are used for the treatment of airway diseases with non-infectious origin: glucocorticoids, bronchodilators (beta-2 adrenoceptor agonists and muscarinic antagonists), and mucosolvants (dembrexin and acetylcystein). In addition, antibiotics are administered for infectious airway diseases. Prominent side effects of these standard therapies are tachycardia, mydriasis, change in the hydration status of the mucous mem-branes and colic for bronchodilators and adrenocortical suppression (reduction in the blood serum levels of cortisol), laminitis, hepatopathy, muscle wasting, altered bone metabolism, increased susceptibility to infection (neutrophilia, lymphopenia) and decreased antibody response to vaccination for glucocorticoids (Couetil et al., 2007, Dauvillir et al., 2011).

The problem underlying the present invention is to provide a medication for horses which allows the treatment of airway disease in horses with a quick onset of action while reducing the risk of side effects for the treated animals.

BRIEF SUMMARY OF THE INVENTION

It has been surprisingly found that muscarinic antagonists, especially long-acting muscarinic antagonists (LAMAs), preferably a LAMA of the formula I, are particularly advantageous for the use in a method of treating an airway disease in equines, preferably horses.

Preferred LAMAs have the following general structure:

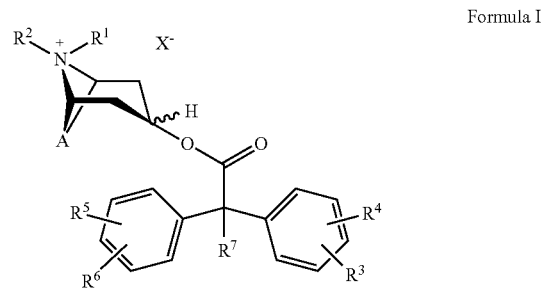

Formula I wherein A denotes a double-bonded group selected from among

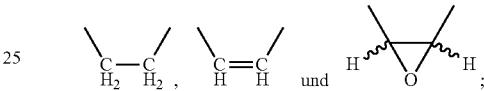

X— denotes an anion with a single negative charge, R1 and R2 denote C1-C4-alkyl, which may optionally be substituted by hydroxy or halogen; R3, R4, R5 and R6, which may be identical or different, denote hydrogen, C1-C4-alkyl, C1-C4-alkyloxy, hydroxy, CF3, CN, NO2 or halogen; R7 denotes hydrogen, C1-C4-alkyl, C1-C4-alkyloxy, C1-C4-alkylene-halogen, halogen-C1-C4-alkyloxy, C1-C4-alkylene-OH, CF3, —C1-C4-alkylene-C1-C4-alkyloxy, —O—COC1-C4-alkyl, —O—COC1-C4-alkyl-halogen, —O—COCF3 or halogen, optionally in the form of the individual optical isomers, mixtures of the individual enantiomers or racemates thereof, while if A denotes

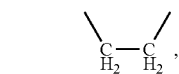

$R^1$ and $R^2$ denote methyl and $^3$, $R^4$, $R^5$ and $R^6$ denote hydrogen, $R^7$ cannot also be hydrogen.

Further, it has been surprisingly found that especially LAMA 1 or another pharmaceutically acceptable salt of the cation thereof or a composition comprising LAMA 1 or a pharmaceutically acceptable salt thereof is particularly advantageous for the use in a method of treating an airway disease in equines, preferably horses.

An advantage of the present invention is the quick start of the effect after administration lasting up to several hours (see for example, Example 7). In addition, the once daily treatment with LAMA 1 for one week is comparable to the significant improvement in lung function after the twice daily administration of clenbuterol for one week. This is accompanied with a significant increase in the arterial blood pH and a significant decrease in the partial pressure of carbon dioxide ($paCO_2$) in the arterial blood, which are observed only after the administration of LAMA 1 for one week.

Furthermore, it has been surprisingly found that a combination of a muscarinic antagonist, especially of a long-acting muscarinic antagonist (LAMA), preferably a LAMA of the formula I, most preferably LAMA 1 or another pharmaceutically acceptable salt of the cation thereof, and a glucocorticoid such as ciclesonide or a pharmaceutically acceptable salt thereof is particularly advantageous for the use in a method of treating an airway disease in equines, preferably horses. An advantage of the present invention is the quick onset of the effect after the administration of the combination.

Additionally, it has been surprisingly found that a (triple) combination of a muscarinic antagonist, especially of a long-acting muscarinic antagonist (LAMA), preferably a LAMA of the formula I, most preferably LAMA 1 or another pharmaceutically acceptable salt of the cation thereof, and a glucocorticoid such as ciclesonide or a pharmaceutically acceptable salt thereof and optionally/or a long-acting beta-2 adrenergic agonist (LABA) or a pharmaceutically acceptable salt thereof, is particularly advantageous for the use in a method of treating an airway disease in equines, preferably horses. An advantage of the present invention is the great extent of the effect after the administration of the (triple) combination.

LAMA 1 improves lung function, increases blood pH and reduces $paCO_2$, whereas both LABAs and/or LAMAs in general improve lung function and clinical score, whereas ciclesonide improves lung function and clinical score as well.

LAMA 1 is currently not approved in equine or any other species. Clenbuterol is approved in equine to be used for treatment of airways diseases accompanied by bronchospasm.

Although both LAMAs and LABAs in general as well as glucocorticoids such as ciclesonide are used separately as medication against pulmonary diseases in certain species, it is surprising that the above described combination(s) (such as double or triple combinations of LAMAs, glucocorticoids and optionally LABAs or a combination of LAMAs and LABAs, preferably the combination of a LAMA, most preferably LAMA 1, and a glucocorticoid, most preferably ciclesonide) actually leads to a quick and extensive relief during equine pulmonary diseases such as RAO, IAD and SPAOPD. Some combinations are known in human medicine for the treatment of asthma and/or chronic obstructive pulmonary disease (e.g. SYMBICORT® TURBOHALER® containing budesonide and formoterol). However, these combinations have not been shown to be effective in equines such as horses so far.

The advantage of the above described combination(s) (muscarinic antagonist/LAMA, preferably LAMA 1, and a glucocorticoid, preferably ciclesonide, as well as triple combinations with a LABA or a combination of a LAMA, preferably LAMA 1, and a LABA) compared to the use of a glucocorticoid such as ciclesonide or budesonide or fluticasone alone is that the onset of the effect is quick (within minutes after the administration of the combination).

An additional advantage of the combination therapy (such as the combinations described above, especially the combination of a LAMA, preferably LAMA 1, and a glucocorticoid, preferably ciclesonide) compared for example to the use of a LAMA alone is that the observed (technical/therapeutic) effect is greater for the combination.

DETAILED DESCRIPTION OF THE INVENTION

Figure 1:
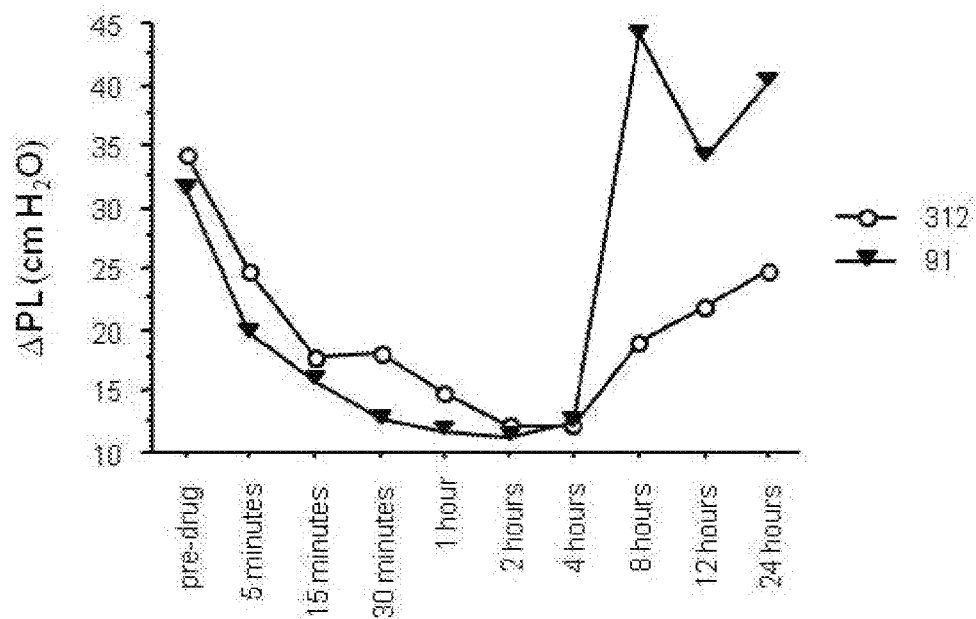
FIG. 1: Phase I: Temporal variations of transpulmonary pressure (ΔPL) in two individual horses (horse ID 312 and 91) following a single administration of 800 μg LAMA 1.

Before describing the various aspects of the present invention it shall be noted that as used herein and in the appended claims, the singular forms "a", "an", and "the" include plural reference unless the context clearly dictates otherwise. Thus, for example, reference to "a preparation" includes a plurality of such preparations reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as re-ported in the publications which might be used in connection with the invention. Nothing herein is to be construed as an admission that the invention is not entitled to antedate such disclosure by virtue of prior invention. Terms not specifically defined herein should be given the meanings that would be given to them by one of skill in the art in light of the disclosure and the context. As used in the specification, however, unless specified to the contrary, the following terms have the meaning indicated and the following conventions are adhered to.

Muscarinic Antagonists: The term "muscarinic antagonists" refers to a group of substances that block the effects of acetylcholine on muscarinic receptors to reverse airway obstruction [Barnes, 2004]. Therefore "muscarinic antagonists" are also often denoted as "anticholinergics" or "anticholinergic agents".

Examples for muscarinic antagonists include ipratropium bromide (which is often administered in equine medicine), atropine, aclidinium bromide, umeclidinium and glycopyrrolate.

The following subgroups of muscarinic antagonists can be defined:
1. long-acting muscarinic antagonists" or "LAMAs";
2. short-acting muscarinic antagonists" or "SAMAs".

An example of a LAMA is glycopyrrolate. An example of a SAMA is atropine.

The term "long-acting muscarinic antagonists" or "LAMAs" refers to a group of substances that block the effects of acetylcholine on muscarinic receptors for a longer period of time. Examples for LAMAs include tiotropium bromide or anticholinergics of the following general formula I:

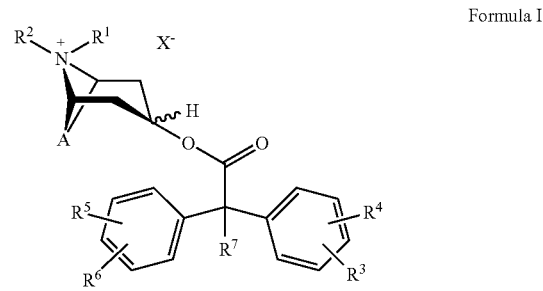

Formula I wherein
A denotes a double-bonded group selected from among

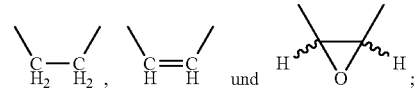

X— denotes an anion with a single negative charge,
$R^1$ and $R^2$ denote $C_1$-$C_4$-alkyl, which may optionally be substituted by hydroxy or halogen;
$R^3$, $R^4$, $R^5$ and $R^6$, which may be identical or different, denote hydrogen, $C_1$-$C_4$-alkyl, $C_1$-$C_4$-alkyloxy, hydroxy, CF3, CN, NO2 or halogen;
R7 denotes hydrogen, $C_1$-$C_4$-alkyl, $C_1$-$C_4$-alkyloxy, $C_1$-$C_4$-alkylene-halogen, halogen-$C_1$-$C_4$-alkyloxy, $C_1$-$C_4$-alkylene-OH, CF3, —$C_1$-$C_4$-alkylene-$C_1$-$C_4$-alkyloxy, —O—CO$C_1$-$C_4$-alkyl, —O—CO$C_1$-$C_4$-alkyl-halogen, —O—COCF$_3$ or halogen, optionally in the form of the individual optical isomers, mixtures of the individual enantiomers or racemates thereof, while if A denotes

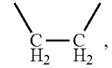

$R^1$ and $R^2$ denote methyl and
$R^3$, $R^4$, $R^5$ and $R^6$ denote hydrogen,
$R^7$ cannot also be hydrogen.

Anticholinergics of the general formula I and processes for preparing them are disclosed for example in WO02/32899, which is hereby incorporated therein.

LAMA 1: The term "LAMA 1" describes a novel anticholinergic agent with the chemical name (1α,2β,4β,5α,7β)-3-Oxa-9-azoniatricyclo[3.3.1.0$^{2,4}$] nonane, 9,9-dimethyl-7-(1-oxo-2,2-diphenylpropoxy)-bromide or alternatively (short name) scopine 2,2-diphenylpropionate methobromide.

LAMA 1 (=scopine 2,2-diphenylpropionate methobromide) has the following chemical structure:

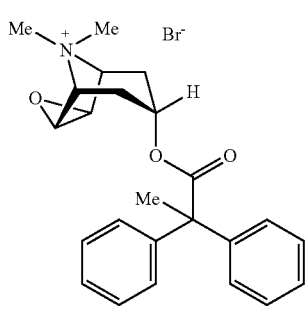

Formula II

LAMA 1 has the sum formula $C_{24}H_{28}NO_3$*Br and has a molecular weight of 458.39 g/mol.

LAMA 1 is further characterized as follows:

| scopine 2,2-diphenyl-propionate methobromide | | Mean $K_D$ [nM] Hm3 | Diss. t1/2 [h] Hm3 | Effects in the Kallos-Pagel Model vs. tiotropium |
|---|---|---|---|---|
| [structure] | Br⁻ | 0,4 | 0,4 | 3 to 10 fold lower efficacy (acute), 10 fold lower efficacy (chronic), protection over 24 hours (acute and chronic) |

Beta-2 Adrenoceptor Agonists: The term "beta-2 adrenoreceptor agonists" or "beta-2 adrenergic agonists" refers to a group of substances that stimulate β2-adrenergic receptors to relax airway smooth muscles [Tashkin and Fabbri, 2010].

The following subgroups of "beta-2 adrenoreceptor agonists" or "beta-2 adrenergic agonists" can be defined:
1. "long-acting beta-2 adrenergic agonists" or "LABAs";
2. "short-acting beta-2 adrenergic agonists" or "SABAs".

The term "long-acting beta-2 adrenergic agonists" or "LABAs" refers to a subgroup of substances that stimulate β2-adrenergic receptors to relax airway smooth muscles for a longer period of time.

Examples for LABAs include salmeterol, formoterol, bambuterol, indacaterol, vilanterol, abediterol and olodaterol hydrochloride.

Examples for beta-2 adrenoreceptor agonists of the SABA type include salbutamol or albuterol, clenbuterol, pirbuterol and fenoterol.

Glucocorticoids: The term "glucocorticoid" refers to a class of steroid hormones that bind to the glucocorticoid receptor (GR), which is present in almost every vertebrate animal cell. The name glucocorticoid (glucose+cortex+steroid) derives from its role in the regulation of the metabolism of glucose, its synthesis in the adrenal cortex, and its steroidal structure.

Glucocorticoids are part of the feedback mechanism in the immune system that turns immune activity (inflammation) down. They are therefore used in medicine to treat diseases caused by an overactive immune system, such as allergies, asthma, autoimmune diseases, and sepsis.

Preferred glucocorticoids according to the present invention are ciclesonide and/or budesonide and/or fluticasone.

The term "ciclesonide" ((11β,16α)-16,17-[[(R)-Cyclohexylmethylene]bis(oxy)]-11-hydroxy-21-(2-methyl-1-oxopropoxy)pregna-1,4-diene-3,20-dione, $C_{32}H_{44}O_7$, $M_r$=540.7 g/mol) is well known in the art and means/describes a glucocorticoid used to treat asthma and allergic rhinitis in humans. It is marketed for application in humans under the brand name ALVESCO® (Takeda GmbH) for asthma and OMNARIS®/OMNAIR® (Takeda GmbH) for hay fever in the US and Canada. Ciclesonide is a prodrug. It is transformed into the active metabolite C21-C21-desisobutyrylciclesonide (=desciclesonide) via hydrolysis by intracellular esterases in the lung. Ciclesonide is a non-halogenated glucocorticoid, which predominantly exists in its form as R-Enantiomer.

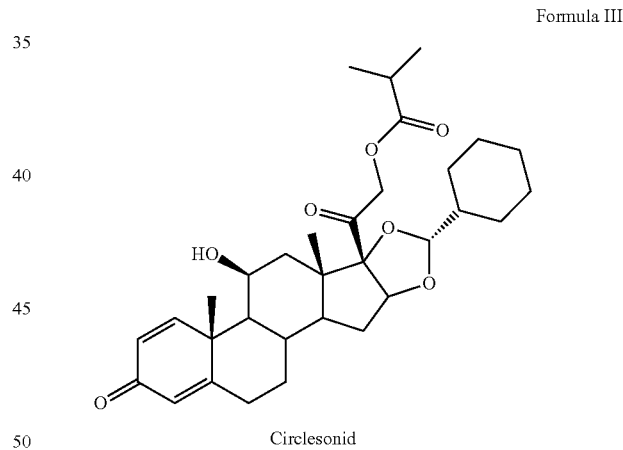

Formula III

Circlesonid

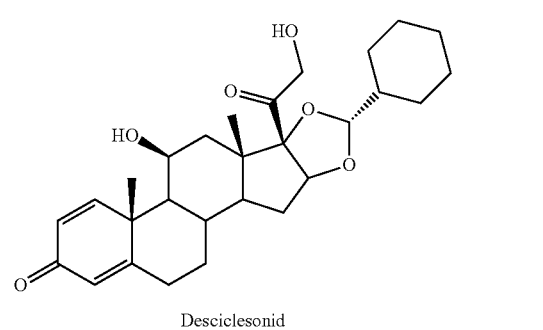

Formula IV

Desciclesonid

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound (also called the active metabolite), for example, by hydrolysis in blood or by activation via oxidation as in case of thioether groups. Most common prodrugs include esters and amide analogues of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can usually be readily prepared from the parent compounds using methods known in the art.

The term "equine" means of or belonging to the family Equidae, which includes the horses, asses, and zebras, preferably horses. In addition, the term "equine" encompasses also hybrids of members of the family Equidae (e.g., mules, hinnies, etc.)

The term "patient" or "subject" embraces mammals such as primates including humans. The term "patient" or "subject" as used herein relates specifically to horses, especially horses suffering from airway disease (particularly pulmonary disease), preferably from recurrent airway obstruction (RAO) also called heaves or equine COPD and/or summer pasture associated obstructive pulmonary disease (SPAOPD) also called Summer Pasture Associated Recurrent Airway Obstruction (SPARAO) and/or inflammatory airway disease (IAD), most preferably from RAO.

The term "airway disease" in horses means the following: recurrent airway obstruction (RAO) also called heaves or equine COPD, Summer Pasture Associated Obstructive Pulmonary disease (SPAOPD), inflammatory airway disease (IAD), exercise induced pulmonary hemorrhage (EIPH), infectious diseases, chronic interstitial lung disease and upper respiratory tract functional disorders.

The term "pulmonary disease" means: recurrent airway obstruction (RAO) also called heaves or equine COPD, Summer Pasture Associated Obstructive Pulmonary disease (SPAOPD), inflammatory airway disease (IAD), exercise induced pulmonary hemorrhage (EIPH), infectious diseases, or chronic interstitial lung disease.

The term "recurrent airway obstruction (RAO)" in horses means the following: a chronic syndrome of mature horses with reversible airway obstruction in the stable showing periods of laboured breathing at rest during exacerbation.

The term "Summer Pasture Associated Obstructive Pulmonary disease (SPAOPD)" in horses means the following: a chronic syndrome, which shares many clinical and pathological similarities with RAO at rest on the pasture, suggesting similar pathogenesis, however, it is caused by different antigens.

The term "inflammatory airway disease (IAD)" in horses means the following: a chronic syndrome of horses showing poor performance or coughing or excess tracheal mucus without showing periods of laboured breathing at rest.

The term "effective amount" as used herein means an amount sufficient to achieve a reduction of airway disease in a horse when ciclesonide is administered at a dosage as described herein. The progress of the therapy (improvement of airway disease, particularly pulmonary disease, preferably recurrent airway obstruction (RAO) and/or Summer Pasture Associated Obstructive Pulmonary disease (SPAOPD) and/or inflammatory airway disease (IAD), most preferably RAO as described herein) can be monitored by standard airway/pulmonary diagnosis, for example, by clinical examination, airway fluid cytology, endoscopy, lung function measurement, or blood-gas analysis.

The term "pharmaceutically acceptable derivative thereof" means but is not limited to pharmaceutically acceptable salts, derivatives, metabolites or pro-drugs of a drug. Derivatives as used herein include but are not limited to, any hydrate forms, solvates, isomers, enantiomers, racemates, racemic conglomerate and the like of the compound of choice. Suitable pharmaceutically acceptable salts are well known in the art and may be formed with an inorganic or organic acid, such as hydrochloric acid, hydrobromic acid, sulfuric acid, phosphoric acid, nitric acid, ace-tic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

The term "pharmaceutically acceptable excipient (or carrier or adjuvants)" for use with the pharmaceutical composition(s) according to the present invention include, for example, ion exchangers, alumina, aluminum stearate, lecithin, serum proteins, buffer substances, water, salts or electrolytes and cellulose-based substances. This is not a complete list possible pharmaceutically acceptable carriers, excipients and/or adjuvants, and one of ordinary skilled in the art would know other possibilities, which are replete in the art.

A pharmaceutical composition/preparation/medicament according to the invention may contain solvents such as water and/or ethanol, acidifiers such as hydrochloric acid, citric acid and/or phosphoric acid, and other excipients like preservatives such as benzalkonium chloride or ethanol, or stabilizers such as EDTA, butylhydroxyanisole or butylhydroxytoluene, viscosity modifiers such as hydroxypropyl methyl cellulose, or solubilizers such as hydroxypropyl-beta-cyclodextrin, or substances to make the application of the composition more pleasant to the animals such as aromas or flavors.

The concentrations of each solvent can range between 1% m/V and 100% m/V, the concentration of the other excipients can range from 0.01% m/V to 10% m/V.

Administration: Suitable forms for "administration" of LAMA 1 or combinations of glucocorticoids such as ciclesonide with LAMA 1 or other LAMAs and/or beta-2 adrenoreceptor agonist such as long-acting beta-2 adrenergic agonist (LABAs) are for example inhalation, parenteral or oral administration, preferably inhalation.

In the specific administration via the RESPIMAT® inhaler (Boehringer Ingelheim International GmbH) the content of the pharmaceutically effective LAMA 1 should be in the range from 0.2 to 7% m/V, preferably 0.3 to 6.0% m/V or 0.4 to 5% m/V of the total composition, i.e. in amounts which are sufficient to achieve the dose range specified hereinafter.

When administered by inhalation ciclesonide may be given as an ethanolic solution or a solution containing a mixture of water and ethanol. Preferably, therefore, pharmaceutical formulations are characterised in that they comprise ciclesonide according to the preferred aspects above.

It is particularly preferred that the combination is administered via inhalation/ex inhaler, preferably it is administered once or twice a day. The administration of the combination can be performed by one inhaler containing both components of the combination. In addition, the administration of the combination can be performed subsequently by two inhalers, each of them containing one of the components of the combination. The subsequent administrations can be performed with or without a break between the administrations of the individual components. Suitable formulations may be obtained, for example, by mixing LAMA 1 with known excipients, for example water, pharmaceutically acceptable organic solvents such as mono- or polyfunctional alcohols (e.g. ethanol or glycerol), or refrigerants/propellants such as hydrofluoroalkanes (HFA), specifically HFA 227 and HFA 134a. For a liquid formulation, additional excipients for example hydrochloric acid or citric acid to adjust the [H$^+$] concentration may be added.

It is especially preferred that LAMA 1 is administered by/via an aqueous/ethanolic droplet inhaler, for example the RESPIMAT® inhaler or another inhalation device using the RESPIMAT® aerosol-generating technology. Preferably LAMA 1 is administered once or twice a day. For this purpose, LAMA 1 has to be made available in a liquid solution which is suitable for the inhaler.

Most preferably the solvent in the liquid formulation (inhalation solution) comprises either water alone, or a mixture of <95% V/V ethanol and 5% V/V water, such as 90% V/V ethanol and 10% V/V water.

A further aspect of the present invention is the application of the liquid formulation (inhalation solution) using the RESPIMAT® inhaler or another inhalation device using the RESPIMAT® aerosol-generating technology. The RESPIMAT® inhaler is disclosed for example in WO 97/12687, which is hereby incorporated therein. This inhaler can advantageously be used to produce the inhalable aerosols according to the invention. The dose of active substance delivered ex RESPIMAT® inhaler can be calculated from:

- the concentration of active substance in the liquid formulation [µg/µL],
- the "delivered volume", defined as the volume of liquid expelled from the RESPIMAT® inhaler per actuation [µL]. The delivered volume ex RESPIMAT® inhaler has been found to be approximately 11 µL, per actuation, according to the following formula:

Dose [µg]=Concentration [µg/µL]·Delivered Volume [µL]

In the context of the present invention the term "dose" means the delivered dose "ex inhaler".

In a further aspect of the present invention the composition is administered via an (equine) inhaler device. Suitable (equine) inhaler devices comprise for example a pressurized metered dose inhaler (pMDI) or an aqueous/ethanolic droplet inhaler. A specific form of an aqueous/ethanolic droplet inhaler is for example the RESPIMAT® inhaler or another inhalation device using the RESPIMAT® technology. Preferably, the (equine) inhaler device comprises/consists of an aerosol generating core based on the RESPIMAT® aerosol-generating technology, and other parts to adapt the inhaler to equine use. An (equine) inhaler device is disclosed for example in WO2010149280, which is hereby incorporated therein.

In a preferred aspect the composition is an aqueous formulation and is administered via an (equine) inhaler device.

In a further aspect of the present invention the liquid formulation comprises one or more of the solvents/propellants: water, ethanol, hydrofluoroalkane(s) such as HFA 227 and HFA 134a, hydrofluoroolefin(s) such as HFO-1234ze, and optionally additional excipients. HFA is an abbreviation for hydrofluoroalkane and HFO is an abbreviation for hydrofluoroolefin.

In addition to formulations containing LAMA 1 alone, additional compositions containing in addition a glucocorticoid and/or LABA are possible. To achieve such a combination formulation a solvent consisting of ethanol in addition to water to increase the solubility of the individual drug substances can be used. Such a solvent can contain up to 95% V/V ethanol and as little as 5% V/V water. Solvents containing ethanol have the additional advantage of requiring a lower concentration or no preservative as combinations of ethanol and water can inhibit the growth or kill microorganisms.

The invention relates to muscarinic antagonists (including long acting muscarinic antagonists (LAMAs)), preferably of the general formula I, more preferably of the formula II (=LAMA 1), for the treatment of airway disease, such as pulmonary disease, preferably recurrent airway obstruction (RAO), summer pasture associated obstructive pulmonary disease (SPAOPD), and inflammatory airway disease (IAD) in animals such as equines, preferably horses.

The invention further relates to a combination of a muscarinic antagonists (including long acting muscarinic antagonists (LAMAs), preferably of the general formula I, more preferably of the formula II (=LAMA 1), with a glucocorticoid such as ciclesonide or budesonide, preferably ciclesonide, for the treatment of airway disease, such as pulmonary disease, preferably recurrent airway obstruction (RAO), summer pasture associated obstructive pulmonary disease (SPAOPD), and inflammatory airway disease (IAD) in animals such as equines, preferably horses.

The invention further relates to a combination of a muscarinic antagonists (including long acting muscarinic antagonists (LAMAs), preferably of the general formula I, more preferably of the formula II (=LAMA 1), with a glucocorticoid such as ciclesonide or budesonide, and optionally with beta-2 adrenoceptor agonists (including long acting beta-2 adrenoceptor agonists (LABAs)) for the treatment of airway disease, such as pulmonary disease, preferably recurrent airway obstruction (RAO), summer pasture associated obstructive pulmonary disease (SPAOPD), and inflammatory airway disease (IAD) in animals such as equines, preferably horses.

The invention further relates to a combination of a muscarinic antagonists (including long acting muscarinic antagonists (LAMAs), preferably of the general formula I, more preferably of the formula II (=LAMA 1), with a glucocorticoid such as ciclesonide or budesonide, or with beta-2 adrenoceptor agonists (including long acting beta-2 adrenoceptor agonists (LABAs)) for the treatment of airway disease, such as pulmonary disease, preferably recurrent airway obstruction (RAO), summer pasture associated obstructive pulmonary disease (SPAOPD), and inflammatory airway disease (IAD) in animals such as equines, preferably horses.

Preferably said beta-2 adrenoceptor agonist is salbutamol (albuterol), pirbuterol, clenbuterol, fenoterol, salmeterol, formoterol, indacaterol, vilanterol, abediterol and olodaterol (hydrochloride).

In a further aspect of the present invention the LAMA of the present invention is glycopyrrolate, ipratropium bromide, aclidinium bromide, umeclidinium or tiotropium bromide.

The invention specifically concerns a long-acting muscarinic antagonist (LAMA) or another pharmaceutically acceptable salt of the cation thereof for use as a medicament in an Equine, such as a horse.

The invention concerns a long-acting muscarinic antagonist (LAMA) or another pharmaceutically acceptable salt of the cation thereof for the use in a method of treating an airway disease in an equine, preferably a horse.

Preferably the LAMA is a compound of the general formula:

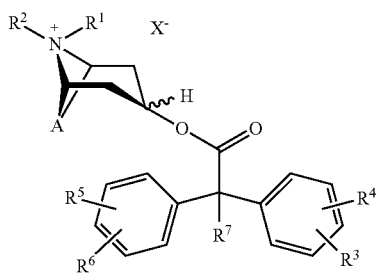

wherein
A denotes a double-bonded group selected from among

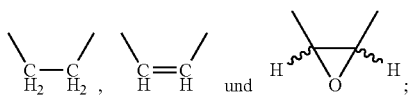

X— denotes an anion with a single negative charge,
$R^1$ and $R^2$ denote $C_1$-$C_4$-alkyl, which may optionally be substituted by hydroxy or halogen;
$R^3$, $R^4$, $R^5$ and $R^6$, which may be identical or different, denote hydrogen, $C_1$-$C_4$-alkyl, $C_1$-$C_4$-alkyloxy, hydroxy, CF3, CN, NO2 or halogen;
R7 denotes hydrogen, $C_1$-$C_4$-alkyl, $C_1$-$C_4$-alkyloxy, $C_1$-$C_4$-alkylene-halogen, halogen-$C_1$-$C_4$-alkyloxy, $C_1$-$C_4$-alkylene-OH, CF3, —$C_1$-$C_4$-alkylene-$C_1$-$C_4$-alkyloxy, —O—CO$C_1$-$C_4$-alkyl, —O—CO$C_1$-$C_4$-alkyl-halogen, —O—COCF$_3$ or halogen, optionally in the form of the individual optical isomers, mixtures of the individual enantiomers or racemates thereof, while if A denotes

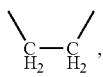

$R^1$ and $R^2$ denote methyl and
$R^3$, $R^4$, $R^5$ and $R^6$ denote hydrogen,
$R^7$ cannot also be hydrogen.

More preferably the LAMA is a compound of the formula (LAMA 1):

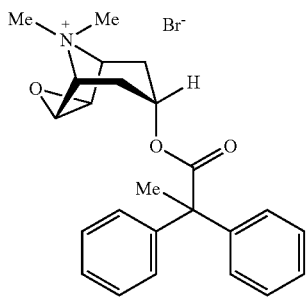

In a specific aspect of the present invention the concentration of LAMA 1 ranges between 0.2 to 7% m/V, preferably 0.3 to 6.0% m/V or 0.4 to 5% m/V of the total composition.

The invention concerns a long-acting muscarinic antagonist (LAMA) or another pharmaceutically acceptable salt of the cation thereof or a pharmaceutical composition comprising a LAMA or another pharmaceutically acceptable salt of the cation thereof, in combination with a glucocorticoid such as ciclesonide or budesonide or fluticasone (preferably ciclesonide) or a pharmaceutical composition comprising ciclesonide or budesonide or fluticasone or a pharmaceutically acceptable salt thereof for use as a medicament in an Equine such as a horse.

The invention further concerns a long-acting muscarinic antagonist (LAMA) or another pharmaceutically acceptable salt of the cation thereof or a pharmaceutical composition comprising a LAMA or another pharmaceutically acceptable salt of the cation thereof, in combination with a glucocorticoid such as ciclesonide or a pharmaceutical composition comprising ciclesonide or a pharmaceutically acceptable salt thereof for use in a method of treating an airway disease in an equine, preferably a horse.

In a specific aspect of the present invention the pharmaceutical composition comprising the LAMA is a fixed dose combination/a pharmaceutical composition comprising a LAMA or pharmaceutically acceptable salts thereof and a glucocorticoid such as ciclesonide or budesonide or pharmaceutically acceptable salts thereof. A preferred combination is a LAMA of general formula I, most preferred LAMA1, in combination with ciclesonide or budesonide, preferably ciclesonide. Optionally, said pharmaceutical composition comprising the LAMA and the glucocorticoid additionally contains beta-2 adrenoreceptor agonists, such as a LABA.

In another aspect of the present invention the LAMA and the glucocorticoid are further combined with beta-2 adrenoreceptor agonists, such as a LABA or pharmaceutically acceptable salts thereof. These compounds or part of them may be formulated either as separate pharmaceutical compositions or as fixed dose combinations.

In a preferred aspect of the present invention the LAMA is a compound of the general formula:

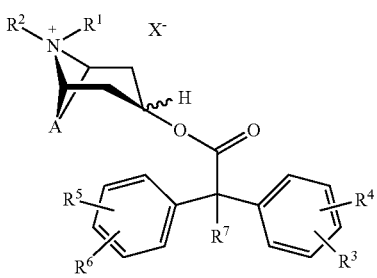

wherein
A denotes a double-bonded group selected from among

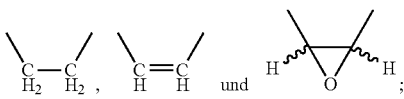

X— denotes an anion with a single negative charge,
$R^1$ and $R^2$ denote $C_1$-$C_4$-alkyl, which may optionally be substituted by hydroxy or halogen;
$R^3$, $R^4$, $R^5$ and $R^6$, which may be identical or different, denote hydrogen, $C_1$-$C_4$-alkyl, $C_1$-$C_4$-alkyloxy, hydroxy, CF3, CN, NO2 or halogen;
R7 denotes hydrogen, $C_1$-$C_4$-alkyl, $C_1$-$C_4$-alkyloxy, $C_1$-$C_4$-alkylene-halogen, halogen-$C_1$-$C_4$-alkyloxy, $C_1$-$C_4$-alkylene-OH, CF3, —$C_1$-$C_4$-alkylene-$C_1$-$C_4$-alkyloxy, —O—CO$C_1$-$C_4$-alkyl, —O—CO$C_1$-$C_4$-alkyl-halogen, —O—COCF$_3$ or halogen, optionally in the form of the individual optical isomers, mixtures of the individual enantiomers or racemates thereof, while if A denotes

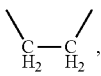

$R^1$ and $R^2$ denote methyl and
$R^3$, $R^4$, $R^5$ and $R^6$ denote hydrogen, $R^7$ cannot also be hydrogen.
Preferably the LAMA is a compound of the formula (LAMA 1):

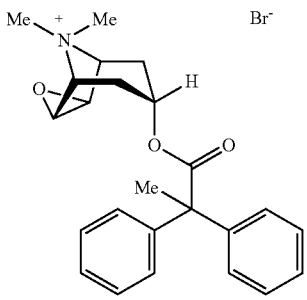

In a specific aspect of the present invention the concentration of LAMA 1 ranges between 0.2 to 7% m/V, preferably 0.3 to 6.0% m/V or 0.4 to 5% m/V of the total composition.

A specific aspect of the present invention is the combination of LAMA 1 or a pharmaceutically acceptable salt thereof with ciclesonide or a pharmaceutically acceptable salt thereof.

Another specific aspect of the present invention is the combination of LAMA 1 or a pharmaceutically acceptable salt thereof with budesonide or a pharmaceutically acceptable salt thereof.

A further aspect of the present invention is the combination of LAMA 1 or a pharmaceutically acceptable salt thereof with clenbuterol or a pharmaceutically acceptable salt thereof.

Another specific aspect of the present invention is the combination of LAMA 1 or a pharmaceutically acceptable salt thereof with ciclesonide or a pharmaceutically acceptable salt thereof and albuterol/albuterol sulfate or another pharmaceutically acceptable salt thereof.

A further specific aspect of the present invention is the combination of LAMA 1 or a pharmaceutically acceptable salt thereof with ciclesonide or a pharmaceutically acceptable salt thereof and olodaterol hydrochloride or another pharmaceutically acceptable salt thereof.

In another specific aspect of the present invention the LAMA is tiotropium bromide or a pharmaceutically acceptable salt thereof. A specific aspect of the present invention is the combination of tiotropium bromide with ciclesonide and optionally olodaterol hydrochloride.

In a specific aspect of the present invention the airway disease is a pulmonary disease. Preferably the airway disease is selected from the group consisting of: recurrent airway obstruction (RAO), summer pasture associated obstructive pulmonary disease (SPAOPD), and inflammatory airway disease (IAD).

In a further specific aspect of the present invention said LAMA or the pharmaceutical composition comprising the LAMA is (in) a liquid formulation, preferably a partially ethanolic formulation, most preferably said liquid formulation is for inhalation.

In another specific aspect of the present invention said LAMA or the pharmaceutical composition comprising the LAMA is administered via an (equine) inhaler device, preferably said inhaler device comprises:
a. a pressurized metered dose inhaler or an aqueous/ethanolic droplet inhaler such as the RESPIMAT® inhaler or another inhalation device using the RESPIMAT® aerosol-generating technology and
b. an adapter for equine use.

In a preferred aspect of the present invention LAMA 1 or a pharmaceutically acceptable salt of the cation thereof is administered at a dose of 100 µg to 3000 µg ex inhaler, 200 µg to 2000 µg ex inhaler, 200 µg to 800 µg ex inhaler, preferably at a dose of 200 µg to 800 µg ex inhaler.

In another preferred aspect of the present invention ciclesonide or a pharmaceutical composition comprising ciclesonide or a pharmaceutically acceptable salt thereof is administered at a dose of 100 µg to 5000 µg ex inhaler, 450 µg to 3712.5 µg ex inhaler, 900 µg to 3712.5 µg ex inhaler, preferably at a dose of 900 µg to 3712.5 µg ex inhaler.

In a further preferred aspect of the present invention the LAMA or the pharmaceutical composition comprising the LAMA is administered once or twice a day (once or twice daily), preferably once a day.

The invention further concerns a pharmaceutical composition comprising a long-acting muscarinic antagonist (LAMA) or pharmaceutically acceptable salts thereof and a LABA or pharmaceutically acceptable salts thereof and optionally a glucocorticoid such as ciclesonide or budesonide (preferably ciclesonide) or pharmaceutically acceptable salts thereof and optionally a pharmaceutically acceptable excipient.

The invention furthermore concerns a pharmaceutical composition comprising a long-acting muscarinic antagonist (LAMA) or pharmaceutically acceptable salts thereof and a glucocorticoid such as ciclesonide or budesonide (preferably ciclesonide) or pharmaceutically acceptable salts thereof and optionally a LABA or pharmaceutically acceptable salts thereof and optionally a pharmaceutically acceptable excipient.

Preferably said composition is a liquid formulation, most preferably a solution for inhalation.

In a preferred aspect of this invention the LAMA is a compound of the general formula

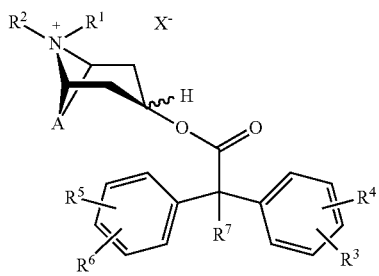

wherein

A denotes a double-bonded group selected from among

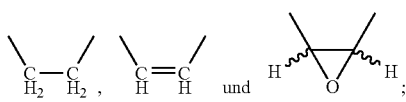

X— denotes an anion with a single negative charge, $R^1$ and $R^2$ denote $C_1$-$C_4$-alkyl, which may optionally be substituted by hydroxy or halogen;

$R^3$, $R^4$, $R^5$ and $R^6$, which may be identical or different, denote hydrogen, $C_1$-$C_4$-alkyl, $C_1$-$C_4$-alkyloxy, hydroxy, CF3, CN, NO2 or halogen;

R7 denotes hydrogen, $C_1$-$C_4$-alkyl, $C_1$-$C_4$-alkyloxy, $C_1$-$C_4$-alkylene-halogen, halogen-$C_1$-$C_4$-alkyloxy, $C_1$-$C_4$-alkylene-OH, CF3, —$C_1$-$C_4$-alkylene-$C_1$-$C_4$-alkyloxy, —O—CO$C_1$-$C_4$-alkyl, —O—CO$C_1$-$C_4$-alkyl-halogen, —O—COCF$_3$ or halogen, optionally in the form of the individual optical isomers, mixtures of the individual enantiomers or racemates thereof, while if A denotes

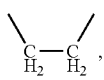

$R^1$ and $R^2$ denote methyl and
$R^3$, $R^4$, $R^5$ and $R^6$ denote hydrogen,
$R^7$ cannot also be hydrogen.

Most preferably the LAMA is a compound of the formula (LAMA 1):

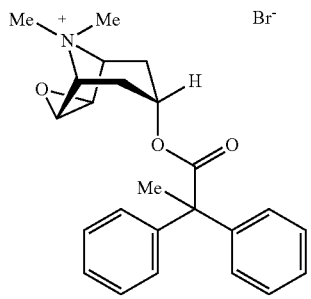

In a specific aspect of the present invention the concentration of LAMA 1 ranges between 0.2 to 7% m/V, preferably 0.3 to 6.0% m/V or 0.4 to 5% m/V of the total composition.

The invention further concerns a method of treating an airway disease in an equine, preferably a horse, comprising
a. administrating a therapeutically effective amount of a LAMA or a pharmaceutical composition comprising the LAMA or
b. administrating a therapeutically effective amount of a pharmaceutical composition comprising a LAMA or a pharmaceutically acceptable salt thereof in combination with a glucocorticoid such as ciclesonide or a pharmaceutically acceptable salt thereof or
c. administrating a therapeutically effective amount of a pharmaceutical composition comprising a LAMA or a pharmaceutically acceptable salt thereof in combination with a beta-2 adrenoreceptor agonists such as a LABA or a pharmaceutically acceptable salt thereof or
d. administrating a therapeutically effective amount of a pharmaceutical composition comprising a LAMA or a pharmaceutically acceptable salt thereof in combination with a glucocorticoid such as ciclesonide or a pharmaceutically acceptable salt thereof and a beta-2 adrenoreceptor agonists such as a LABA or a pharmaceutically acceptable salt thereof or
e. administrating a therapeutically effective amount of the pharmaceutical composition according to the invention (fixed dose combination)

to an equine patient in need thereof, whereby said airway disease is preferably a pulmonary disease, most preferably said airway disease is selected from the group consisting of: recurrent airway obstruction (RAO), summer pasture associated obstructive pulmonary disease (SPAOPD), and inflammatory airway disease (IAD). Preferably the LAMA is LAMA 1 or a pharmaceutical composition comprising LAMA 1 or another pharmaceutically acceptable salt of the cation thereof.

EXAMPLES

The following examples serve to further illustrate the present invention; but the same should not be construed as a limitation of the scope of the invention disclosed herein.

The following examples 1 to 6 give examples of compositions which are possible to be administered using an inhaler based on the RESPIMAT® spray generating technology.

Example 1

LAMA 1 can be formulated either as an aqueous solution or as an ethanolic solution. This first table shows examples for an aqueous solution:

TABLE 1

| Component | Concentration [g/100 mL] | |
| --- | --- | --- |
| | 0.446% | 0.844% |
| LAMA 1 | 0.446 | 0.844 |
| | 0.541 | 1.022 |
| Benzalkonium chloride | 0.010 | 0.010 |
| Edetate disodium | 0.010 | 0.010 |
| HCl (0.1 M) | ad pH 4.0 | ad pH 4.0 |
| Water | ad 100.0 mL | ad 100.0 mL | where the concentration of hydrogen ions [H⁺] can be measured, for example, by potentiometric titration.

Example 2

LAMA 1 can be formulated either as an aqueous solution or as an ethanolic solution. This second table shows an example of formulations for an ethanolic solution with 50% V/V ethanol

TABLE 2

| Component | Concentration [g/100 mL] | |
| --- | --- | --- |
| | 0.844% | 4.22% |
| LAMA 1 | 0.844 | 4.22 |
| | 1.022 | 5.11 |
| HCl (0.1 M) corresponds to | 0.1 | 0.1 |
| $-\log_{10} c_{H^+}$ | 4.0 | 4.0 |
| 50% V/V ethanol/water | ad 100.0 mL | ad 100.0 mL |

Example 3

The next table shows an example of LAMA 1 formulations for an ethanolic solution with 90% V/V ethanol:

TABLE 3

| Component | Concentration [g/100 mL] | |
| --- | --- | --- |
| | 0.844% | 4.22% |
| LAMA 1 | 0.844 | 4.22 |
| | 1.022 | 5.11 |
| HCl (0.1 M) equivalent to | 0.1 | 0.1 |
| $-\log_{10} c_{H^+}$ | 4.0 | 4.0 |
| 90% V/V ethanol/water | ad 100.0 mL | ad 100.0 mL |

Example 4

LAMA 1 can be formulated as an ethanolic combination formulation with budesonide as shown in the following table 4:

TABLE 4

| Component | Concentration [g/100 mL] | |
| --- | --- | --- |
| | 0.844%/1.810% | 4.22%/1.810% |
| LAMA 1 | 0.844 | 4.22 |
| | 1.022 | 5.11 |
| Budesonide | 1.810 | 1.810 |
| Edetate disodium | 0.001 | 0.001 |
| HCl (0.1 M) equivalent to | 0.1 | 0.1 |
| $-\log_{10} c_{H^+}$ | 4.0 | 4.0 |
| 90% V/V ethanol/water | ad 100.0 mL | ad 100.0 mL |

Example 5

LAMA 1 can be formulated as an ethanolic combination formulation with ciclesonide as shown in the following table 5:

TABLE 5

| Component | Concentration [g/100 mL] | |
| --- | --- | --- |
| | 0.844%/3.00% | 4.22%/1.810% |
| LAMA 1 | 0.844 | 4.22 |
| | 1.022 | 5.11 |
| Ciclesonide | 3.00 | 3.00 |
| Butylhydroxytoluene | 0.05 | 0.05 |
| HCl (0.1 M) equivalent to | 0.1 | 0.1 |
| $-\log_{10} c_{H^+}$ | 4.0 | 4.0 |
| 90% V/V ethanol/water | ad 100.0 mL | ad 100.0 mL |

Example 6

LAMA 1 can be formulated as an ethanolic combination formulation with ciclesonide and albuterol sulfate as shown in the following

TABLE 6

| Component | Concentration [g/100 mL] | |
| --- | --- | --- |
| | 0.84%/3.00%/0.88% | 4.22%/3.00%/0.88% |
| LAMA 1 | 0.84 | 4.22 |
| | 1.02 | 5.11 |
| Ciclesonide | 3.00 | 3.00 |
| Albuterol corresponds to | 0.88 | 0.86 |
| albuterol sulfate | 1.06 | 1.06 |
| Butylhydroxytoluene | 0.1 | 0.1 |
| HCl (0.1M) equivalent to | 0.4 | 0.4 |
| $-\log_{10} c_{H^+}$ | 3.4 | 3.4 |
| 90% V/V ethanol/water | ad 100.0 mL | ad 100.0 mL |

Example 7

Monotherapy with LAMA 1

LAMA 1 is investigated in a study with 4 phases.
LAMA 1 is used in the formulations as described in examples 1 and 2.

Phase I and IV:

LAMA 1 is investigated in two RAO horses at different phases or periods as part of a mouldy hay challenge study. The horses are challenged every day by exposure to mouldy hay. LAMA 1 is administered via the Equine Inhaler device at different doses or formulations. Lung function parameters (change in transpulmonary pressure (ΔPL), lung resistance (RL) and lung elastance (EL)) are measured for 24 h. A single administration of 800 µg LAMA 1 (8 actuations in aqueous formulation) is performed per inhalation to two RAO horses (ID numbers: 312 and 91) in phase I. Two RAO horses are treated with LAMA 1 in phase IV (ID numbers: 40 and 91), which can be divided into three periods. 2000 µg LAMA 1 (20 actuations in aqueous formulation) is administered per inhalation in period 1. 2000 µg LAMA 1 (4 actuations in ethanolic formulation) is administered per inhalation in period 2. 2000 µg LAMA 1 (20 actuations in ethanolic formulation) is administered per inhalation in period 3.

Figure 2:
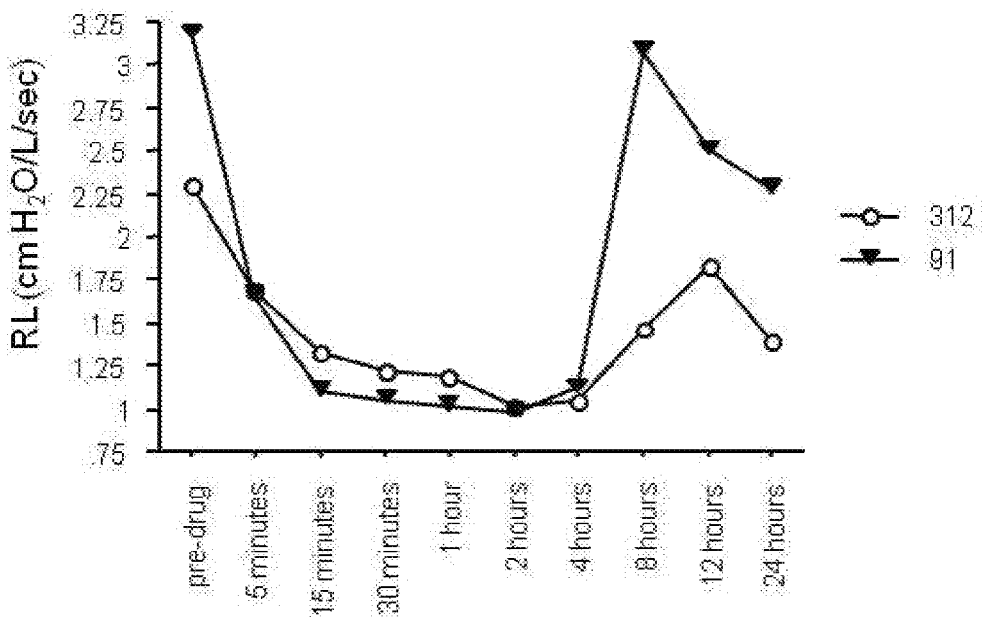
FIG. 2: Phase I: Temporal variations of lung resistance (RL) in two individual horses (horse ID 312 and 91) following a single administration of 800 μg LAMA 1.
Figure 3:
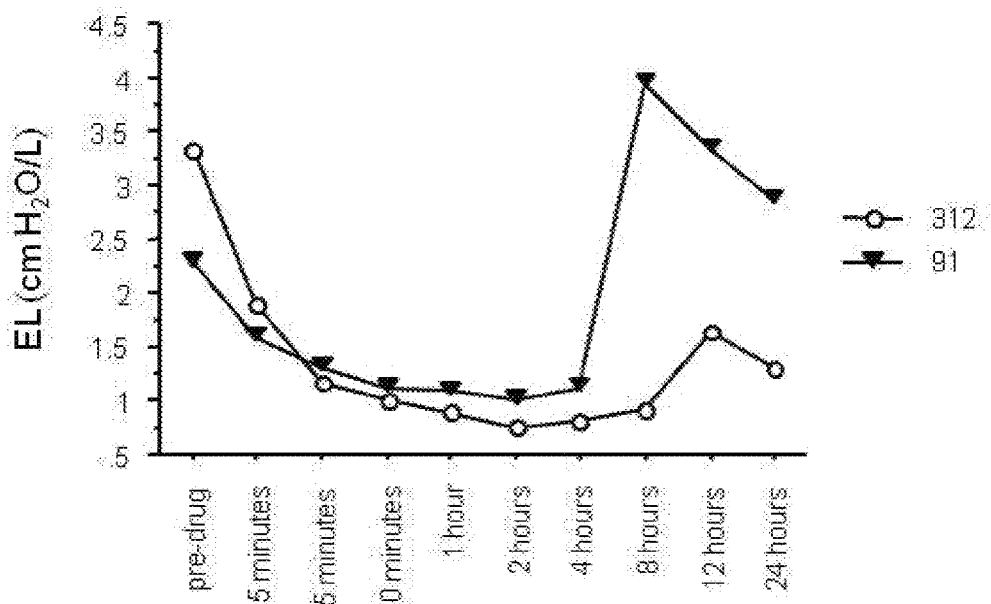
FIG. 3: Phase I: Temporal variations of lung elastance (EL) in two individual horses (horse ID 312 and 91) following a single administration of 800 μg LAMA 1.
Figure 4:
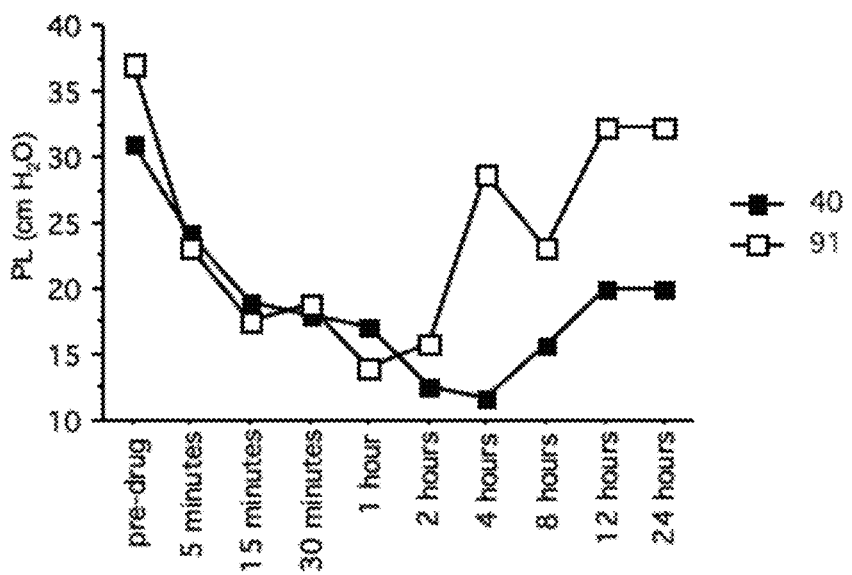
FIG. 4: Phase IV—period 1: Temporal variations of transpulmonary pressure (ΔPL) in two individual horses (horse ID 40 and 91) following a single administration of 2000 μg LAMA 1 (20 puffs, 100 μg/puff in aqueous formulation).
Figure 5:
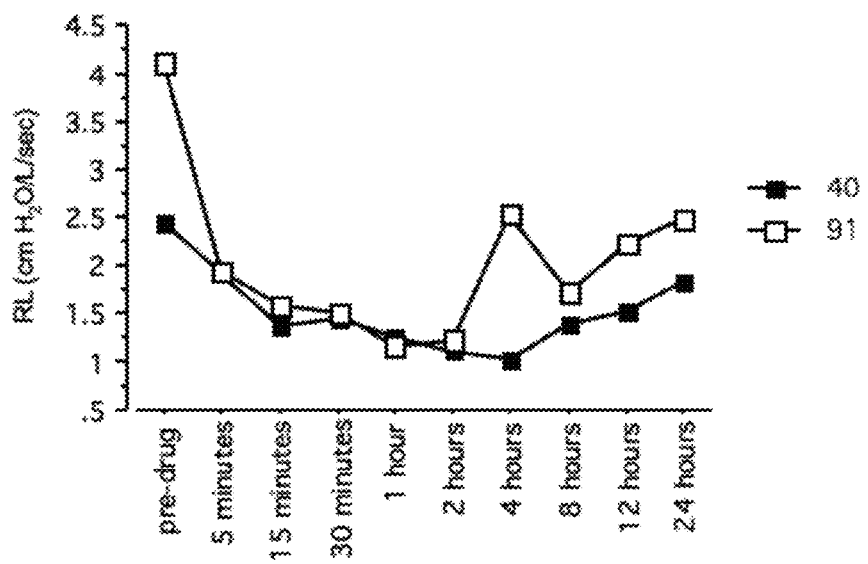
FIG. 5: Phase IV—period 1: Temporal variations of lung resistance (RL) in two individual horses (horse ID 40 and 91) following a single administration of 2000 μg LAMA 1 (20 puffs, 100 μg/puff in aqueous formulation).
Figure 6:
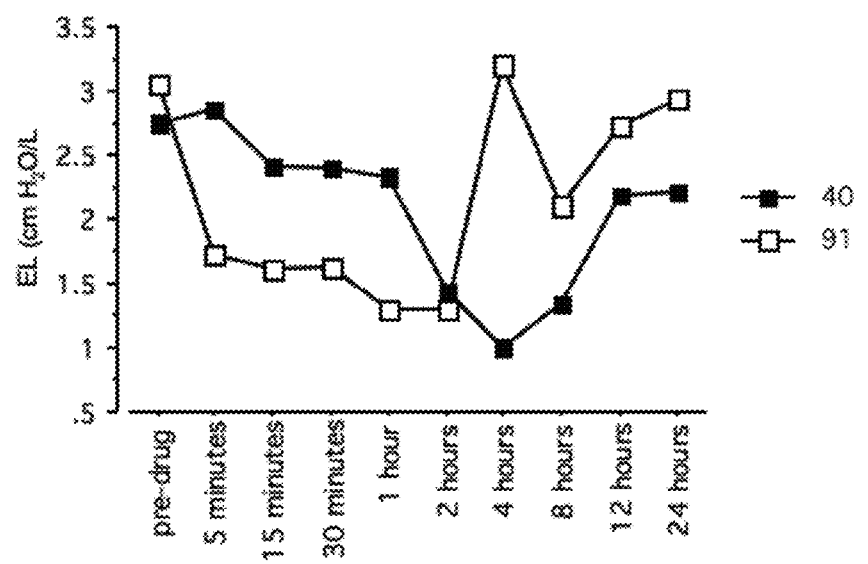
FIG. 6: Phase IV—period 1: Temporal variations of lung elastance (EL) in two individual horses (horse ID 40 and 91) following a single administration of 2000 μg LAMA 1 (20 puffs, 100 μg/puff in aqueous formulation).
Figure 7:
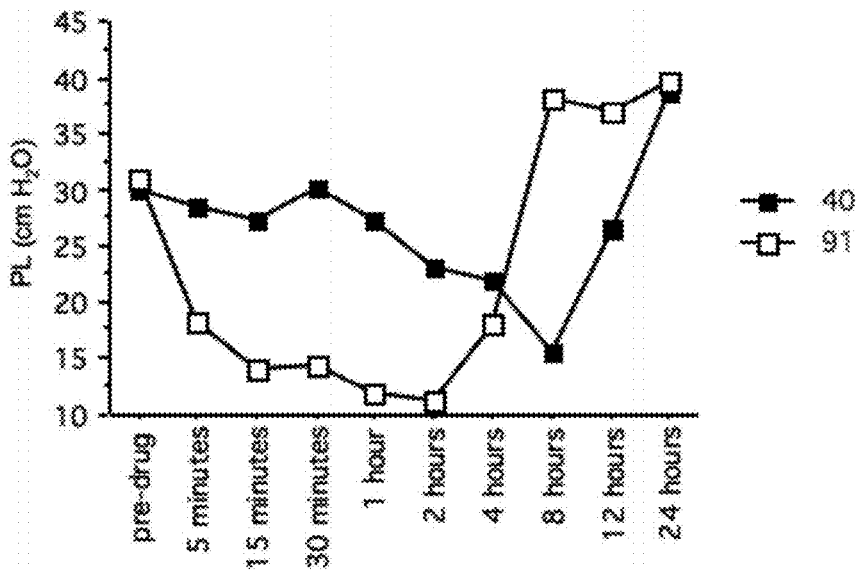
FIG. 7: Phase IV—period 2: Temporal variations of transpulmonary pressure (ΔPL) in two individual horses (horse ID 40 and 91) following a single administration of 2000 μg LAMA 1 (4 puffs, 500 μg/puff in ethanolic formulation).
Figure 8:
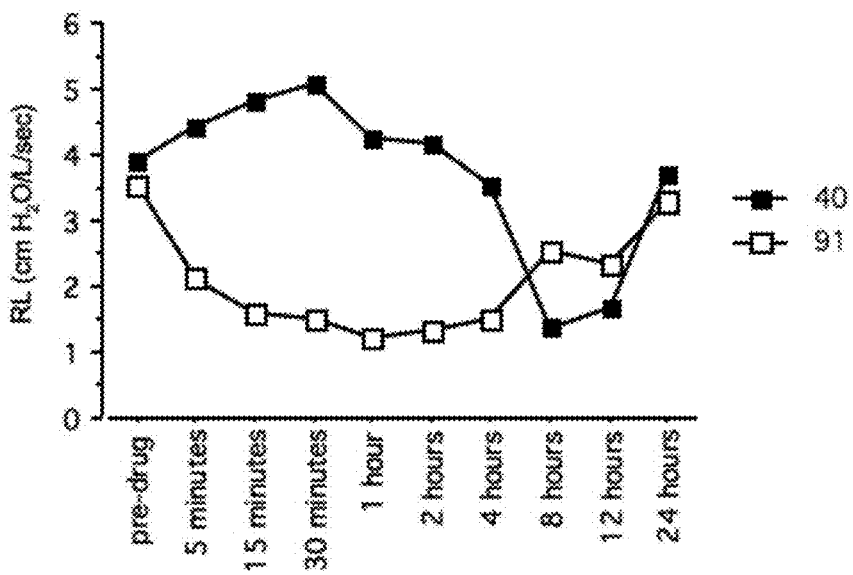
FIG. 8: Phase IV—period 2: Temporal variations of lung resistance (RL) in two individual horses (horse ID 40 and 91) following a single administration of 2000 μg LAMA 1 (4 puffs, 500 μg/puff in ethanolic formulation).
Figure 9:
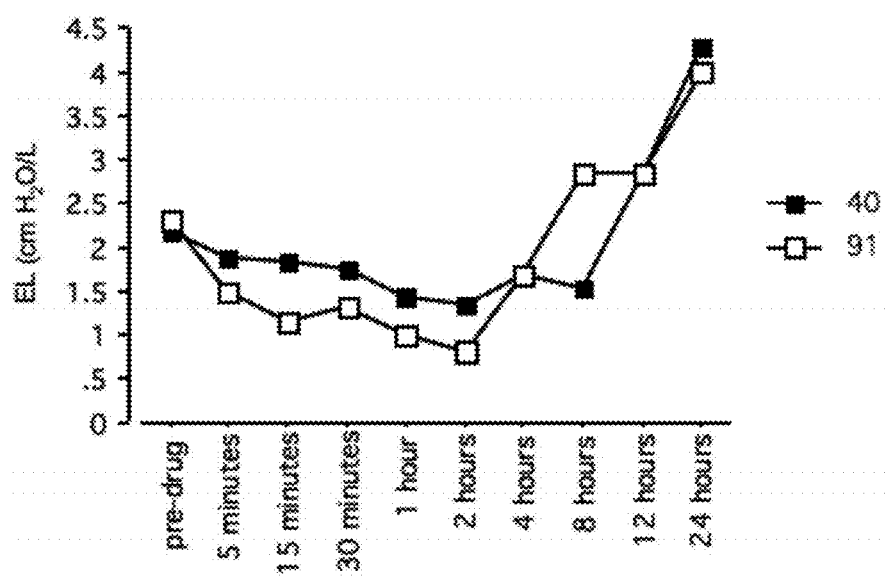
FIG. 9: Phase IV—period 2: Temporal variations of lung elastance (EL) in two individual horses (horse ID 40 and 91) following a single administration of 2000 μg LAMA 1 (4 puffs, 500 μg/puff in ethanolic formulation).
Figure 10:
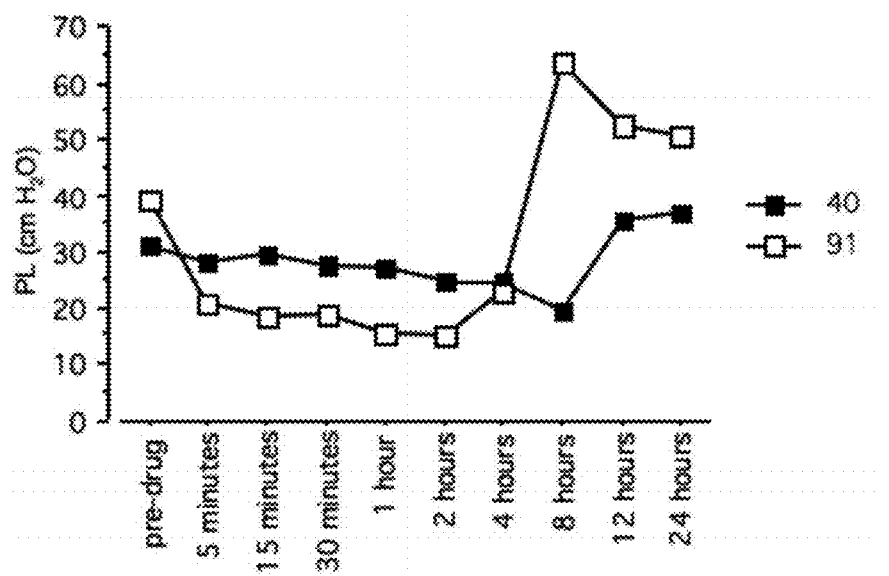
FIG. 10: Phase IV—period 3: Temporal variations of transpulmonary pressure (ΔPL) in two individual horses (horse ID 40 and 91) following a single administration of 2000 μg LAMA 1 (20 puffs, 100 μg/puff in ethanolic formulation).
Figure 11:
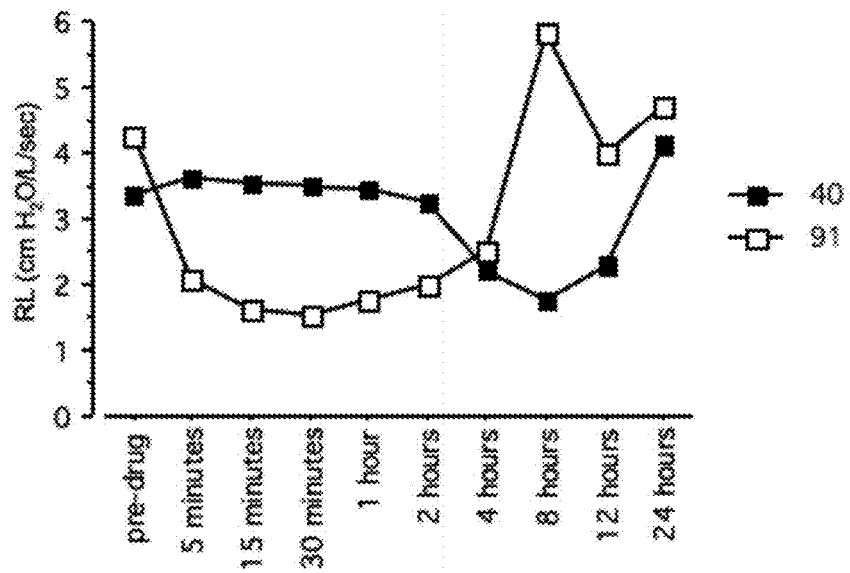
FIG. 11: Phase IV—period 3: Temporal variations of lung resistance (RL) in two individual horses (horse ID 40 and 91) following a single administration of 2000 μg LAMA 1 (20 puffs, 100 μg/puff in ethanolic formulation).
Figure 12:
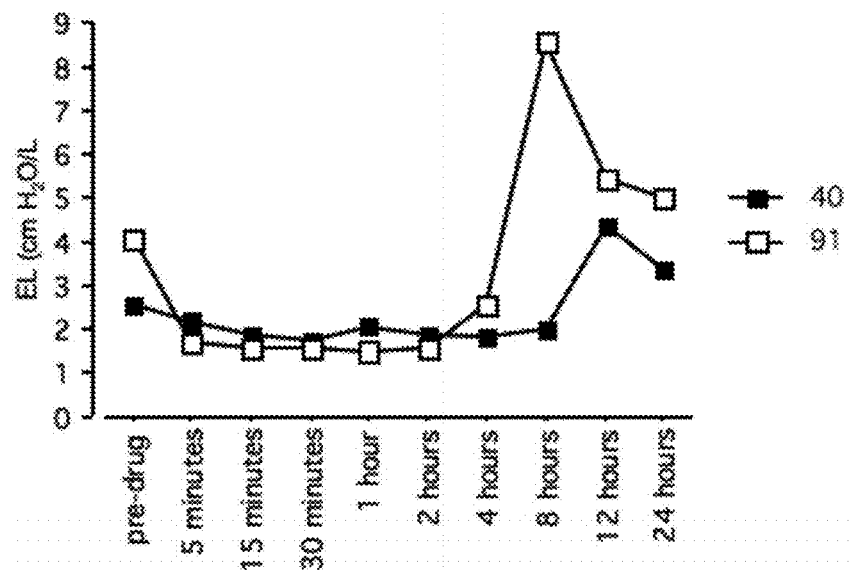
FIG. 12: Phase IV—Period 3: Temporal variations of lung elastance (EL) in two individual horses (horse ID 40 and 91) following a single administration of 2000 μg LAMA 1 (20 puffs, 100 μg/puff in ethanolic formulation).

A decrease is observed in the lung function variables starting 5 minutes after the administration of LAMA 1. The values continue to drop until 2-8 h depending on the lung function parameter, and the dose or formulation of LAMA 1. The lung function variables are below or reach the pre-treatment values at 24 h after the single administration of LAMA 1 (Phase I: FIGS. 1-3; Phase IV, period 1: FIGS. 4-6; Phase IV, period 2: FIGS. 7-9; Phase IV, period 3: FIGS. 10-12).

Phase II:

LAMA 1 is investigated in a cross-over, blinded mouldy hay challenge study. 8 RAO horses are examined in the study, which is divided into an acclimation and a treatment phase. Placebo for LAMA 1 is administered once daily per inhalation via the Equine Inhaler device to all horses for 1 week in the acclimation period. LAMA 1 and clenbuterol are administered to the horses in a cross-over design in the treatment phase. The horses are challenged by exposure to mouldy hay throughout the acclimation and treatment phases. LAMA 1 is administered with the doses of 200 µg (2 actuations)/400 µg (4 actuations)/800 µg (8 actuations)/horse (ex-RESPIMAT®) once daily for 7 days per inhalation via the Equine Inhaler device. Nozzle A and a commercially available RESPIMAT® is used in the study. Clenbuterol is administered with a dose of 0.8 µg/kg per os, twice daily for 7 days. Lung function variables (change in transpulmonary pressure ($\Delta$PL), lung resistance (RL) and lung elastance (EL)), breathing effort score, Borborygmi score, blood gas analysis are examined during the study.

Figure 13:
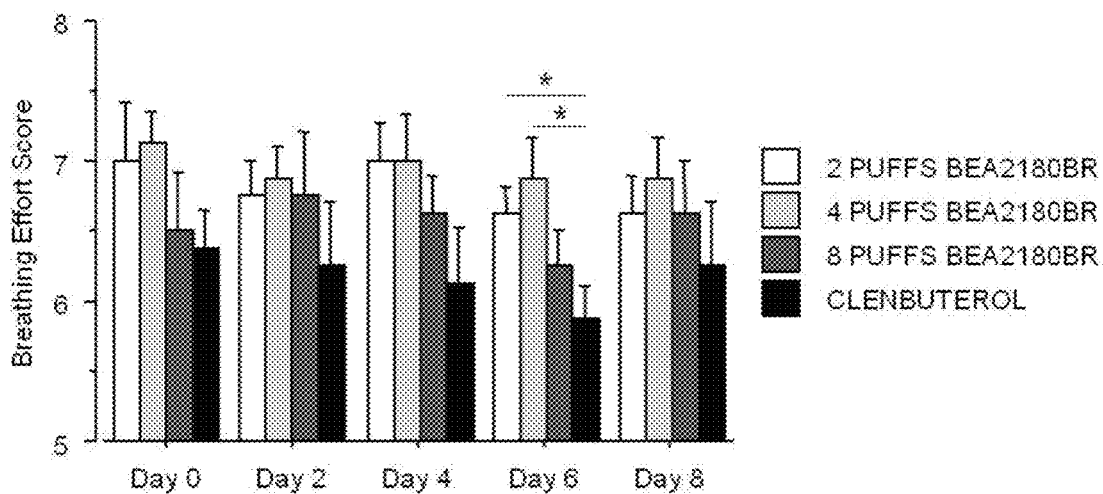
FIG. 13: Phase II: Temporal variations in breathing effort score associated with the administration of clenbuterol (black bars) and three different doses of LAMA 1 (2 puffs: 200 μg (white bars), four puffs: 400 μg (light grey bars) and 8 puffs: 800 μg (dark grey bars) between days 1 and 7 (mean±SEM) (n=8), where SEM is "Standard Error of the Mean".*Significantly different.
Figure 14:
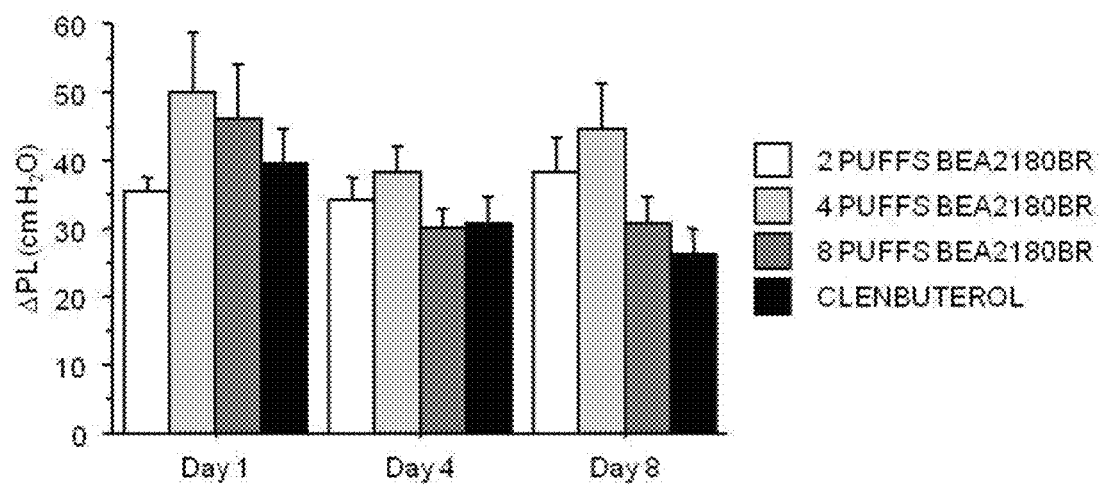
FIG. 14: Phase II: Temporal variations in transpulmonary pressure (ΔPL) associated with the administration of clenbuterol (black bars) and three different doses of LAMA 1 (2 puffs: 200 μg (white bars), four puffs: 400 μg (light grey bars) and 8 puffs: 800 μg (dark grey bars) between days 1 and 7 (mean±SEM) (n=8), where SEM is "Standard Error of the Mean".
Figure 15:
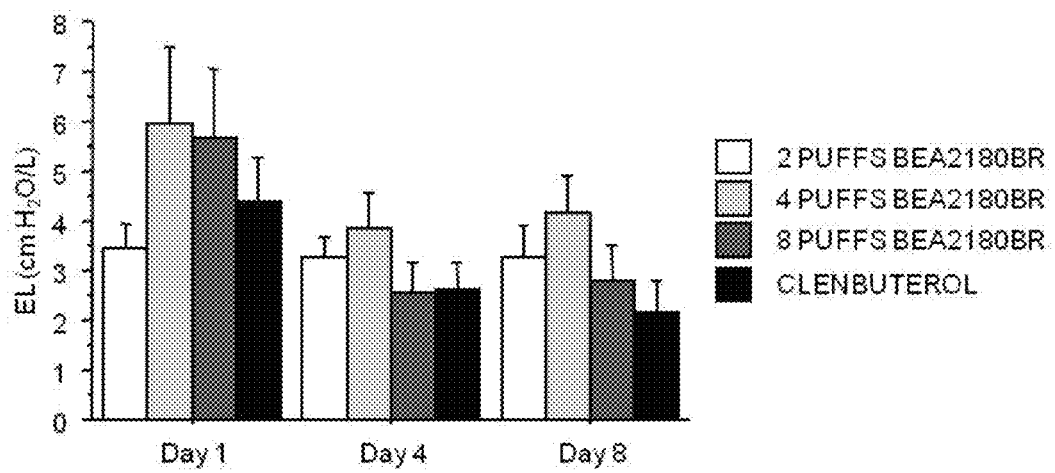
FIG. 15: Phase II: Temporal variations in lung elastance (EL) associated with the administration of clenbuterol (black bars) and three different doses of LAMA 1 (2 puffs: 200 μg (white bars), four puffs: 400 μg (light grey bars) and 8 puffs: 800 μg (dark grey bars) between days 1 and 7 (mean±SEM) (n=8), where SEM is "Standard Error of the Mean".
Figure 16:
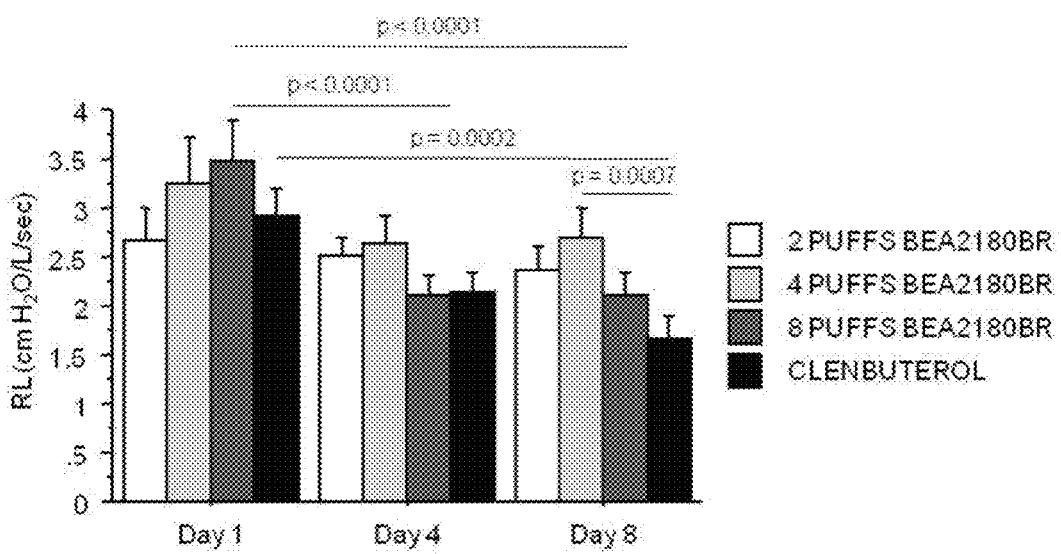
FIG. 16: Phase II: Temporal variations in lung resistance (RL) associated with the administration of clenbuterol (black bars) and three different doses of LAMA 1 (2 puffs: 200 μg (white bars), four puffs: 400 μg (light grey bars) and 8 puffs: 800 μg (dark grey bars) between days 1 and 7 (mean±SEM) (n=8), where SEM is "Standard Error of the Mean".
Figure 17:
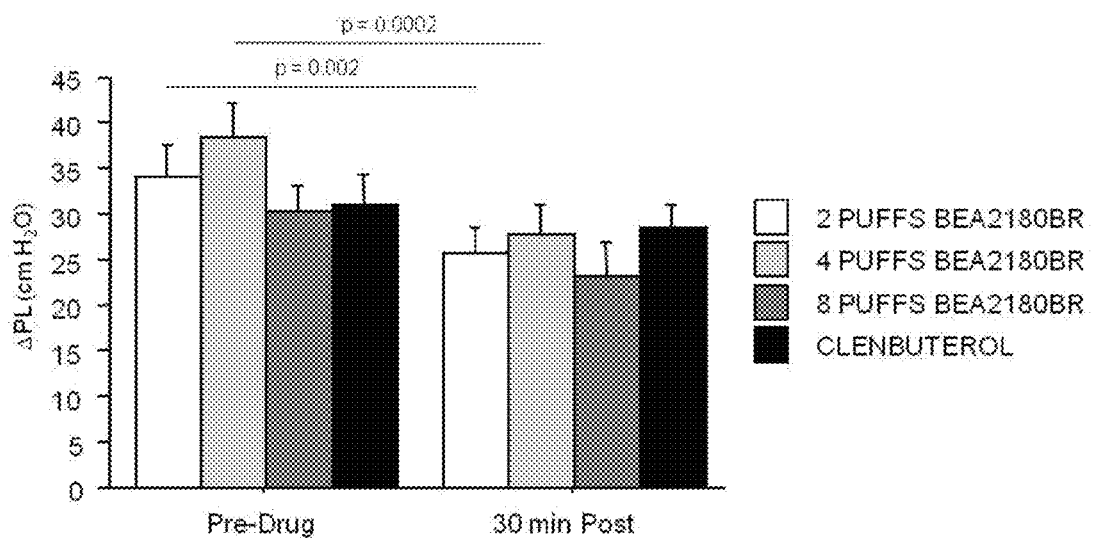
FIG. 17: Phase II: Temporal variations in transpulmonary pressure (ΔPL) before and 30 minutes after the administration of clenbuterol (black bars) and three different doses of LAMA 1 (2 puffs: 200 μg (white bars), four puffs: 400 μg (light grey bars) and 8 puffs: 800 μg (dark grey bars) on Day 4 (mean±SEM) (n=8), where SEM is "Standard Error of the Mean".
Figure 18:
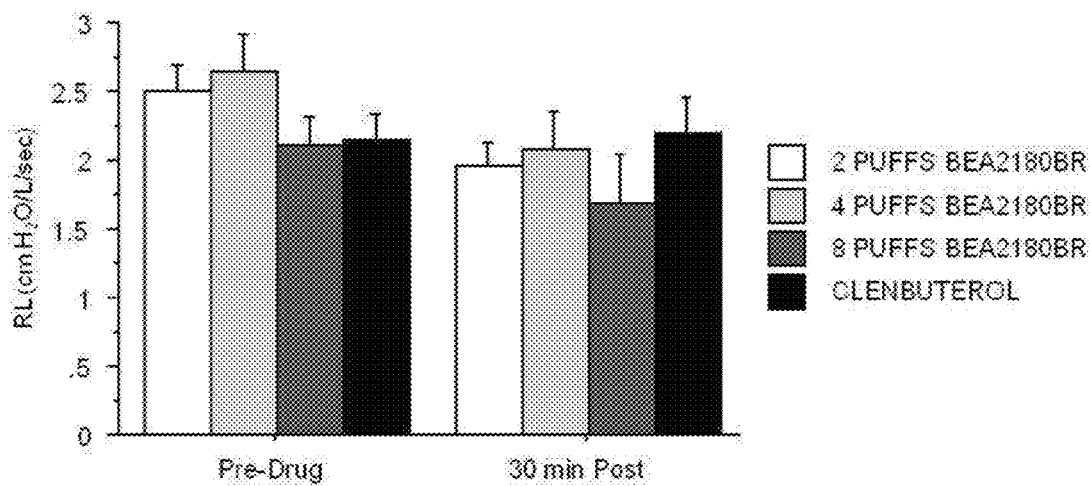
FIG. 18: Phase II: Temporal variations in lung resistance (RL) before and 30 minutes after the administration of clenbuterol (black bars) and three different doses of LAMA 1 (2 puffs: 200 μg (white bars), four puffs: 400 μg (light grey bars) and 8 puffs: 800 μg (dark grey bars) on Day 4 (mean±SEM) (n=8), where SEM is "Standard Error of the Mean".
Figure 19:
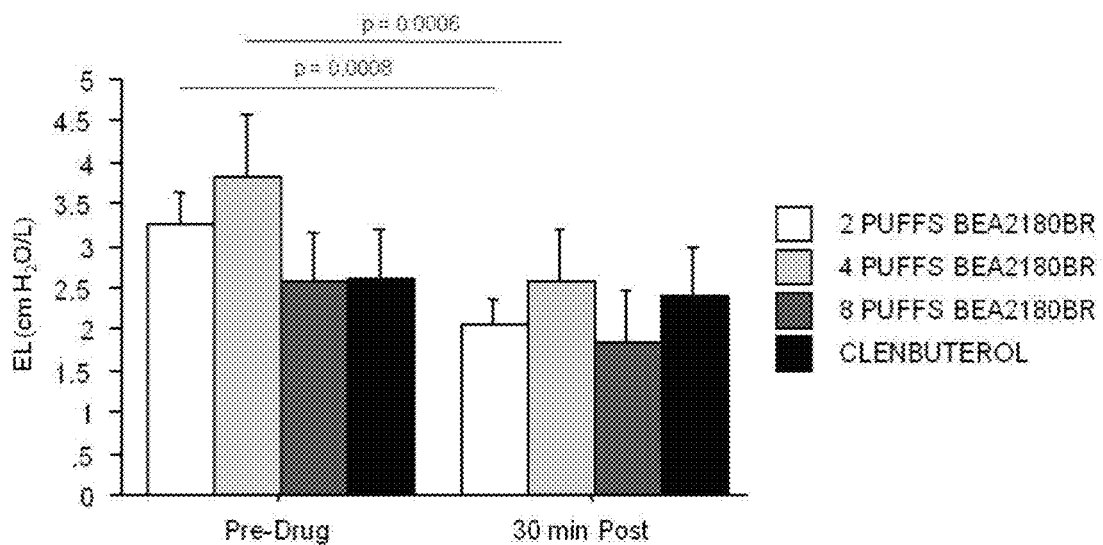
FIG. 19: Phase II: Temporal variations in lung elastance (EL) before and 30 minutes after the administration of clenbuterol (black bars) and three different doses of LAMA 1 (2 puffs: 200 μg (white bars), four puffs: 400 μg (light grey bars) and 8 puffs: 800 μg (dark grey bars) on Day 4 (mean±SEM) (n=8), where SEM is "Standard Error of the Mean".
Figure 20:
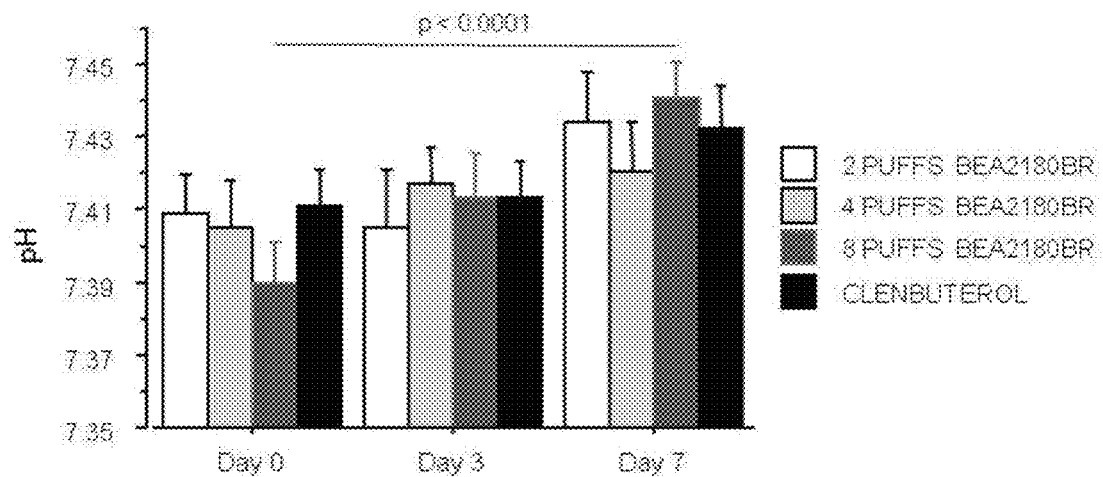
FIG. 20: Phase II: Temporal variations in pH of arterial blood samples associated with the administration of clenbuterol (black bars) and three different doses of LAMA 1 (2 puffs: 200 μg (white bars), four puffs: 400 μg (light grey bars) and 8 puffs: 800 μg (dark grey bars) between days 1 and 7 (mean±SEM) (n=8), where SEM is "Standard Error of the Mean".
Figure 21:
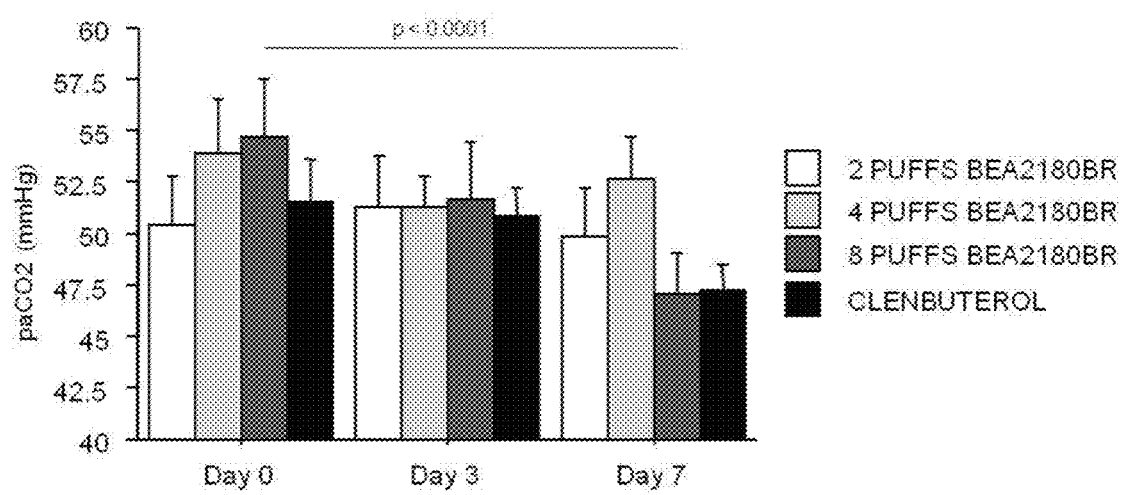
FIG. 21: Phase II: Temporal variations in paCO$_2$ of arterial blood samples associated with the administration of clenbuterol (black bars) and three different doses of LAMA 1 (2 puffs: 200 μg (white bars), four puffs: 400 μg (light grey bars) and 8 puffs: 800 μg (dark grey bars) between days 1 and 7 (mean±SEM) (n=8), where SEM is "Standard Error of the Mean".

Placebo treatment does not induce significant changes on breathing effort score, lung function variables (change in transpulmonary pressure ($\Delta$PL), lung resistance (RL) and lung elastance (EL)), pH, $paCO_2$ and $paO_2$. Clenbuterol treated horses have significantly smaller breathing effort scores on study day 6 than horses treated with 2 or 4 actuations of LAMA 1 (FIG. 13). None of the treatments (LAMA 1 or clenbuterol) alters significantly $\Delta$PL and EL values over time (Days 4 and 8 compared to Day 1) (FIGS. 14 and 15). RL values are significantly reduced over time in the clenbuterol and 800 µg LAMA 1 groups (FIG. 16). Lung function variables are measured before and 30 min after the administration of LAMA 1 on day 4. When compared with pre-treatment values, a decrease in $\Delta$PL, RL and EL is seen in all LAMA 1 groups at 30 min after the administration (FIG. 17-19). The change in $\Delta$PL and EL is statistically significant after the administration of 200 and 400 µg LAMA 1. pH increases and $paCO_2$ reduces significantly in arterial blood in the 800 µg LAMA 1 group on Day 7 compared to Day 0 (FIGS. 20 and 21).

Phase III:

A single administration of 800 µg LAMA 1 (8 actuations in aqueous formulation) is performed per inhalation to two healthy horses in phase III. Subsequently, ECG measurements are done for 48 h. Physiological arrhythmias are noted in both horses before and following the administration of LAMA 1. Only one observation is classified as either a first-degree heart block with aberrant intraventricular repolarization, or an artifact due to the movement of the electrodes.

Example 8

The combination of LAMA 1 and ciclesonide is investigated in a mouldy hay challenge model. 8 RAO horses are treated via inhalation using the Equine Inhaler device. Treatment with LAMA 1 monotherapy (maximum 2000 µg per administration), with ciclesonide monotheraphy (maximum 3212.5 µg per administration) and with the combinations of LAMA 1 and ciclesonide (maximum dose of LAMA 1 is 2000 µg per administration and the maximum dose of ciclesonide is 3712.5 µg per administration) is examined in the study. Lung function variables (change in transpulmonary pressure ($\Delta$PL), lung resistance (RL) and lung elastance (EL)) and weighted clinical score is measured in the study.

An improvement in lung function variables and weighted clinical score is observed in all treatment groups with varying extent. Similarly, the onset of the action shows difference among the treatment groups starting already a few minutes after drug administration.

REFERENCES

1. Kutasi O., Balogh N., Lajos Z., Nagy K., Szenci O. Diagnostic approaches for the assessment of equine chronic pulmonary disorders. J. Eq. Vet. Sci. (2011) 31: 400-410
2. Coutil L. L, Hoffman A. M., Hodgson J., Buechner-Maxwell V., Viel L., Wood J. L. N. and Lavoie J.-P.: Inflammatory airway disease of horses. J. Vet. Intern. Med. (2007) 21: 356-361
3. Dauvillier J., Felippe M. J. B., Lunn D. P., Lavoie-Lamoureux A., Leclere M., Beauchamp G., Lavoie J.-P.: Effect of long-term fluticasone treatment on immune function in horses with heaves. J. Vet. Intern. Med. (2011) 25: 549-557
4. Tashkin D. P. and Fabbri L. M.: Long-acting beta-agonists in the management of chronic obstructive pulmonary disease: current and future agents. Resp. Research (2010) 11:149
5. Barnes P. J.: The role of anticholinergics in chronic obstructive pulmonary disease. Am J Med (2004) 117 (Suppl 12A): 24S-32S.

The invention clamed is:

1. A method of treating an airway disease in an equine, comprising administering to the equine a composition comprising a long-acting muscarinic antagonist (LAMA) or another pharmaceutically acceptable salt of the cation thereof.

2. The method according to claim 1, wherein the LAMA is a compound of the general formula:

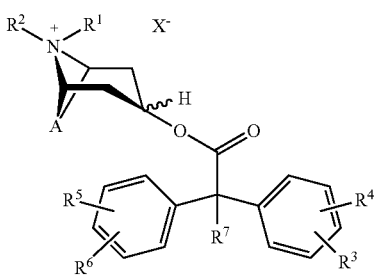

wherein
A denotes a double-bonded group selected from among

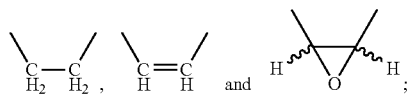

X— denotes an anion with a single negative charge,
$R^1$ and $R^2$ denote $C_1$-$C_4$-alkyl, which may optionally be substituted by hydroxy or halogen;
$R^3$, $R^4$, $R^5$ and $R^6$, which may be identical or different, denote hydrogen, $C_1$-$C_4$-alkyl, $C_1$-$C_4$-alkyloxy, hydroxy, CF3, CN, NO2 or halogen;
R7 denotes hydrogen, $C_1$-$C_4$-alkyl, $C_1$-$C_4$-alkyloxy, $C_1$-$C_4$-alkylene-halogen, halogen-$C_1$-$C_4$-alkyloxy, $C_1$-$C_4$-alkylene-OH, CF3, —$C_1$-$C_4$-alkylene-$C_1$-$C_4$-alkyloxy, —O—COC$_1$-$C_4$-alkyl, —O—COC$_1$-$C_4$-alkyl-halogen, —O—COCF$_3$ or halogen,
optionally in the form of the individual optical isomers, mixtures of the individual enantiomers or racemates thereof, while
if A denotes

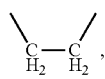

$R^1$ and $R^2$ denote methyl and
$R^3$, $R^4$, $R^5$ and $R^6$ denote hydrogen.

3. The method according to claim 2, wherein the concentration of LAMA ranges between 0.2 to 7% m/V of the composition.

4. The method according to claim 2, wherein the concentration of LAMA ranges between 0.3 to 6.0% m/V of the composition.

5. The method according to claim 2, wherein the concentration of LAMA ranges between 0.4 to 5% m/V of the composition.

6. A method of administering a medicament to an animal, the method comprising administering to the animal a composition comprising a long-acting muscarinic antagonist (LAMA) or another pharmaceutically acceptable salt of the cation thereof in combination with a glucocorticoid.

7. The method according to claim 6, wherein the animal is a mammal.

8. The method according to claim 7, wherein the mammal is an equine.

9. The method according to claim 6, wherein said glucocorticoid is ciclesonide or budesonide or a pharmaceutically acceptable salt thereof.

10. The method according to claim 9, wherein said glucocorticoid is ciclesonide.

11. The method of claim 8, wherein the method of administering further comprises a method for treating the equine for an airway disease.

12. The method according to claim 11, wherein said glucocorticoid is ciclesonide, budesonide, or pharmaceutically acceptable salts thereof.

13. The method according to claim 11, wherein said composition further comprises a beta-2 adrenoreceptor agonist.

14. The method according to claim 13, wherein said beta-2 adrenoreceptor agonist is a long-acting beta-2 adrenergic agonist (LABA) or a pharmaceutically acceptable salt thereof.

15. The method according to claim 11, wherein said pharmaceutical composition further comprises a pharmaceutically acceptable excipient.

16. The method according to claim 11, wherein the LAMA is a compound of the general formula:

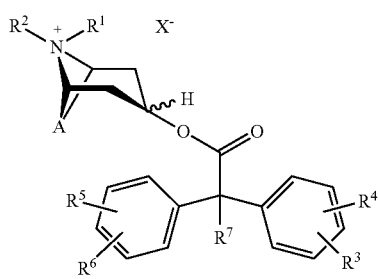

wherein
A denotes a double-bonded group selected from among

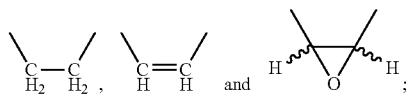

X— denotes an anion with a single negative charge,
$R^1$ and $R^2$ denote $C_1$-$C_4$-alkyl, which may optionally be substituted by hydroxy or halogen;
$R^3$, $R^4$, $R^5$ and $R^6$, which may be identical or different, denote hydrogen, $C_1$-$C_4$-alkyl, $C_1$-$C_4$-alkyloxy, hydroxy, CF3, CN, NO2 or halogen;
R7 denotes hydrogen, $C_1$-$C_4$-alkyl, $C_1$-$C_4$-alkyloxy, $C_1$-$C_4$-alkylene-halogen, halogen-$C_1$-$C_4$-alkyloxy, $C_1$-$C_4$-alkylene-OH, CF3, —$C_1$-$C_4$- alkylene-$C_1$-$C_4$-alkyloxy, —O—COC$_1$-$C_4$-alkyl, —O—COC$_1$-$C_4$-alkyl-halogen, —O—-COCF$_3$ or halogen,
optionally in the form of the individual optical isomers, mixtures of the individual enantiomers or racemates thereof, while
if A denotes

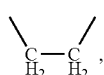

$R^1$ and $R^2$ denote methyl and
$R^3$, $R^4$, $R^5$ and $R^6$ denote hydrogen.

17. The method according to claim 16, wherein the airway disease is a pulmonary disease, preferably the airway disease is selected from the group consisting of: recurrent airway obstruction (RAO), summer pasture associated obstructive pulmonary disease (SPAOPD), and inflammatory airway disease (IAD).

18. The method according to claim 17, wherein said LAMA or the composition comprising the LAMA is in a liquid formulation.

19. The method according to claim 18, wherein said liquid formulation is a partially ethanolic formulation.

20. The method according to claim 18, wherein said liquid formulation is for inhalation.

21. The method according to claim 1, wherein said LAMA or the pharmaceutical composition comprising the LAMA is administered via an inhaler device comprising:
   a. a pressurized metered dose inhaler or an aqueous/ethanolic droplet inhaler; and
   b. an adapter for equine use.

22. The method according to claim 21, wherein said LAMA or the pharmaceutical composition comprising the LAMA is administered as an aerosol via the inhaler device.

23. The method according to claim 21, wherein said LAMA or a pharmaceutically acceptable salt of the cation thereof is administered at a dose of 100 µg to 3000 µg ex inhaler.

24. The method according to claim 21, wherein said dose is 200 µg to 2000 µg ex inhaler.

25. The method according to claim 21, wherein said dose is 200 µg to 800 µg ex inhaler.

26. The method according to claim 21, wherein ciclesonide or a pharmaceutically acceptable salt thereof is administered at a dose of 100 µg to 5000 µg ex inhaler.

27. The method according to claim 21, wherein the dose is 450 µg to 3712.5 µg ex inhaler.

28. The method according to claim 21, wherein the dose is 900 µg to 3712.5 µg ex inhaler.

29. The method according to claim 1, wherein said composition is administered once or twice a day.

30. The method according to claim 1, wherein the LAMA is a compound of the formula (LAMA 1):

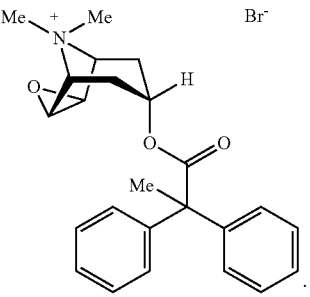

31. The method according to claim 11, wherein the LAMA is a compound of the formula (LAMA 1):

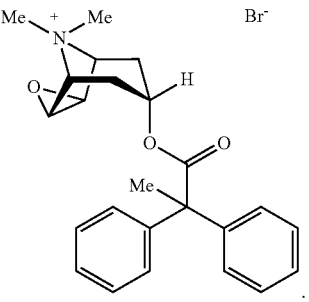

* * * * *